United States Patent [19]

Kula et al.

[11] 4,144,130

[45] Mar. 13, 1979

[54] PROCESS FOR THE SEPARATION OF ENZYMES

[75] Inventors: Maria-Regina Kula; Karl-Heinz Kroner, both of Wolfenbüttel; Wolfgang Stach, Salzgitter-Barum; Helmut Hustedt, Meine, all of Fed. Rep. of Germany; Andija Dureković, Zagreb; Stefica Grandja, Sesvete, both of Yugoslavia

[73] Assignee: Gesellschaft für Biotechnologische Forschung, Braunschweig-Stockheim, Fed. Rep. of Germany

[21] Appl. No.: 787,312

[22] Filed: Apr. 14, 1977

[30] Foreign Application Priority Data

Apr. 14, 1976 [DE] Fed. Rep. of Germany ....... 2616584
Aug. 31, 1976 [DE] Fed. Rep. of Germany ....... 2639129

[51] Int. Cl.$^2$ .............................................. C07G 7/028
[52] U.S. Cl. ................................................... 195/66 R
[58] Field of Search ................................ 195/66 R, 68

[56] References Cited

U.S. PATENT DOCUMENTS

| 3,933,588 | 1/1976 | Dworschack et al. | 195/68 |
| 3,963,575 | 6/1976 | Bulich | 195/66 R X |
| 3,983,008 | 9/1976 | Shinozaki et al. | 195/66 R X |
| 4,016,039 | 4/1977 | Schreiber | 195/66 R |

FOREIGN PATENT DOCUMENTS

2252351 7/1975 France ................................... 195/66 R

OTHER PUBLICATIONS

Biochemistry, vol. 12, No. 13, pp. 2525–2530 (1973).

*Primary Examiner*—Lionel M. Shapiro
*Attorney, Agent, or Firm*—Haseltine, Lake & Waters

[57] ABSTRACT

A process for the recovery of enzymes from intact cells and cell fragments by means of partition in a multiphase system without prior separation of the cell liquid, cell fragments or the cells is described.

37 Claims, 22 Drawing Figures

○ potassium phosphate
□ sodium citrate
△ Tris maleate
× sodium cacodylate
■ sodium acetate
● Tris / HCl ○ potassium phosphate
■ sodium citrate
× sodium cacodylate
● Tris / HCl
□ sodium acetate

PROCESS FOR THE SEPARATION OF ENZYMES

The invention concerns a process for the separation of enzymes from cell-fragments or cells.

The solid-liquid-separation for the separation of cell-fragments or cells from enzyme-solutions is still a technical problem, especially when large volumes have to be handled. Centrifuging and filtering are conventional methods for such separation. Both methods cause difficulties which result from the viscosity of the resulting suspensions, the colloidal nature of the components and the often small density-differences between suspended solid and liquid which lead to low flow-rates (C. F. Naeher & Thum in Spencer, Industrial Aspects of Biochemistry, 1974).

For example in the first step of the separation of pullulanase from *Klebsiella pneumoniae* the enzyme is removed from intact cells with detergents. This step can be carried out without any difficulties on any scale. However, in experiments for the separation of the cells it was found that relatively high g-numbers are necessary which cannot be realized on a technical scale. A separation by filtration is also very difficult because of the detergents present. (With respect to the prior art compare DT-AS 2,245,342.)

From Biochemistry, 1973, volume 12, pages 2525 to 2530, it is known that an enzyme (phospholipase A 1) can be recovered from *Escherichia coli* with the use of a phase-partition-method. According to this method these cells are homogenized, the cell-liquid is separated by centrifuging and then the enzyme dissolved from the cell-membrane. For the phase-distribution multi-phase-systems are used containing polypropyleneglycol, polyethyleneglycol, trimethylaminopolyethyleneglycol, polyethyleneglycolsulfonate, Ficoll and dextran. Besides the fact that this prior art hardly gives any hints for the transfer of the suggested teaching to the recovery of other enzymes it is not possible to carry out the centrifuging of the cell-liquid on a technical scale. This also applies for the phase-partition-methods which are known from Eur. J. Biochem., 1974, Vol. 46, p. 75 to 81, and Eur. J. Biochem., 1974, vol. 48, p. 63 to 69, and which start from either purified enzymes or from yeast-lysate which resulted from centrifuging a homogenized yeast suspension.

It is an object of the invention to provide a process for the recovery of enzymes from cells on a technical scale by which the enzymes can be recovered from disintegrated or intact cells with the use of a partition in a multi-phase-system without any preceding separation of cell-liquid, cell-fragments or cells. This process shall start from any cells in order to separate any enzymes, for example pullulanase (amylopectin-6-glucanohydrolase) and phosphorylase from Klebsiella species, maltase (α-glucosidase) e.g. from brewers yeast-cells (*Saccharomyces carlsbergensis*) and amino-acyl-tRNA-synthetases e.g. from *Escherichia coli*.

It has been found that, surprisingly, a satisfactory separation in aqueous multi-phase-systems can even be achieved in such cases when the cell-liquid has not been separated from the cell-fragments and cells, respectively, in advance.

According to one embodiment of the invention the problem is solved by a process for the separation of enzymes from cell-fragments or cells where the enzymes are solubilized and partitioned together with the cell-fragments and cells, respectively, between different phases of an aqueous multi-phase system containing at least one high-molecular weight compound, the phases are separated from each other and the enzymes separated from the high-molecular weight compounds and (if desired) isolated; this process is characterized in that a multi-phase system is used which contains at least one high-molecular weight compound of the group consisting of unsubstituted or substituted polyalcohols, polyethers, polyesters, polyvinylpyrrolidones and polysaccharides and at least one inorganic salt and that the system which results from the enzyme solubilisation is added together with the enzymes, the insoluble components and the cell liquid into this multi-phase system.

For example a multi-phase-system can be used which contains polyethyleneglycol. In a multi-phase system containing an unsubstituted or substituted polyalcohol or polyether the average molecular weight of these compounds may be smaller than 40,000 and in particular smaller than 10,000.

For example, a multi-phase system can be used which contains a sulphate, e.g. an alkalisulphate and/or a phosphate, e.g. alkaliphosphate, in particular potassium phosphate.

The multi-phase system may for example contain a high-molecular weight compound such as polyethyleneglycol, and a salt such as potassium phosphate. Such a multi-phase system is e.g. suitable for the separation of enzymes from *Escherichia coli*, e.g. aminoacyl-tRNA-synthetases. It is possible to use such systems with such amounts of water, high-molecular weight compounds and salt, that these components by themselves would only form one single phase.

According to another embodiment of the invention the problem is solved by a process for the separation of enzymes from cell-fragments or cells in which the enzymes are solubilized, partitioned together with the cell-fragments and cells, respectively, between different phases of an aqueous multi-phase system containing at least two high-molecular weight compounds of the group consisting of unsubstituted or substituted polyalcohols, polyethers, polyesters, polyvinylpyrrolidones and polysaccharides, the phases being separated from each other and the enzymes separated from the high-molecular weight compounds and (if desired) isolated; this process is characterized in that the system resulting from the enzyme solubilization is added together with the enzymes, the insoluble components and the cell-liquid to the multi-phase-system.

For reasons of economy it is possible to use a multi-phase-system containing polyethyleneglycol and dextran.

As high-molecular weight compounds it is possible to use an unsubstituted or substituted polyalcohol or polyether having a clearly smaller average molecular weight than the enzyme preferably an average molecular weight smaller than 40,000, more preferably smaller than 10,000, most preferably smaller than 6,000, e.g. in the range from 5,000 to 1,550, e.g. about 4,000, and an unsubstituted or substituted polysaccharide having a clearly greater average molecular weight than the enzyme. (Pullulanase has e.g. a molecular weight of about 145,000.)

This may have the result that the enzymes go into the polyalcohol and polyether phase, respectively, and that these high-molecular weight compounds are easily separable from the enzymes, e.g. by ultra-filtration.

In the multiphase-system the total content of polyethyleneglycol can be 1 or more and preferably 4 to 9% by weight and the total content of dextran 0.1 to 15 and preferably 0.1 to 7% by weight.

It is possible to improve the process according to the invention (dependent on the pH) by adding phosphate ions, e.g. orthophosphate (e.g. in form of the different potassium phosphates), pyrophosphate, polyphosphate and/or metaphosphate ions).

The process according to the invention can start from any cells which contain the desired enzyme. For the separation of pullulanase and aminoacyl-tRNA-synthetases it is preferable to use a multiphase-system which contains a high-molecular weight compound and an inorganic salt; for the separation of pullulanase, phosphorylase and maltase it is preferable to use a multiphase-system, containing at least two high-molecular weight compounds.

It is possible to solubilize the enzymes e.g. by disintegration of cells and/or treating them with detergents. Suitable detergents are e.g. triton, cholate, desoxycholate and dodecylsulfate.

Cell-fragments or cells which have not been disintegrated, for example, are considered to be components which are insoluble in the multi-phase system.

In the process according to the invention salts may be present which stem, for example, from detergents or buffers.

It is possible to use every high-molecular weight compound which has hitherto been used in multi-phase systems for the partition of micro-organisms or high-molecular weight biochemical compounds. Reference is made to Albertsson, Partition of Cell Particles and Macromolecules, NY 1971, (and following editions).

Examples of high-molecular weight compounds which can be used in the process according to invention are polypropyleneglycol, polyethyleneglycol, methoxypolyethyleneglycol, trimethylaminopolyethyleneglycol, polyethyleneglycolsulfonate, polyvinylalcohol, polyvinylpyrrolidone, methylcellulose, ethylhydroxyethylcellulose, DEAE-cellulose, alkali metal carboxymethylcellulose, dextran, hydroxypropyldextran, DEAE-dextran, dextransulfate, alkali metal-carboxymethyldextran and Ficoll.

It is possible to use a multi-phase system with a ratio of total volume/cellmass $\geq$ 2 and preferably $\geq$ 5.

Preferably the process is carried out at a pH of 6 to 9 and more preferably 7 to 8.

It is possible to separate the phases on a technical scale, for example, with separators e.g. disc-separators or decanters.

The invention gives evidence that it is possible to separate the phases with the use of commercially available separators even when cell-fragments or cells are simultaneously present. This means for such enzyme-separations a highly developed separator technology which makes possible very high flow rates and avoids an activity loss of enzymes as result of long treatment times.

The suggested liquid/liquid-separation offers the additional benefit that because of the partition between several phases not only insoluble components are separated from the desired enzyme solution but an additional purification can be achieved on the basis of the different K-values of the proteins.

The high-molecular weight compounds which form a multiphase system according to the invention and the proteins introduced by the cells may be separated by methods which are usual in the art. Precipitation of the enzymes or phase-partition, ultrafiltration, dialysis, gel permeation, adsorbents, ion exchangers or electrophoresis are examples.

It is possible to carry out the process according to the invention at room temperature especially when the enzymes are stabilized by the high-molecular weight compounds used.

For a better understanding of these circumstances in the following FIGS. 1 to 16 will be explained in greater detail.

Figure 1:
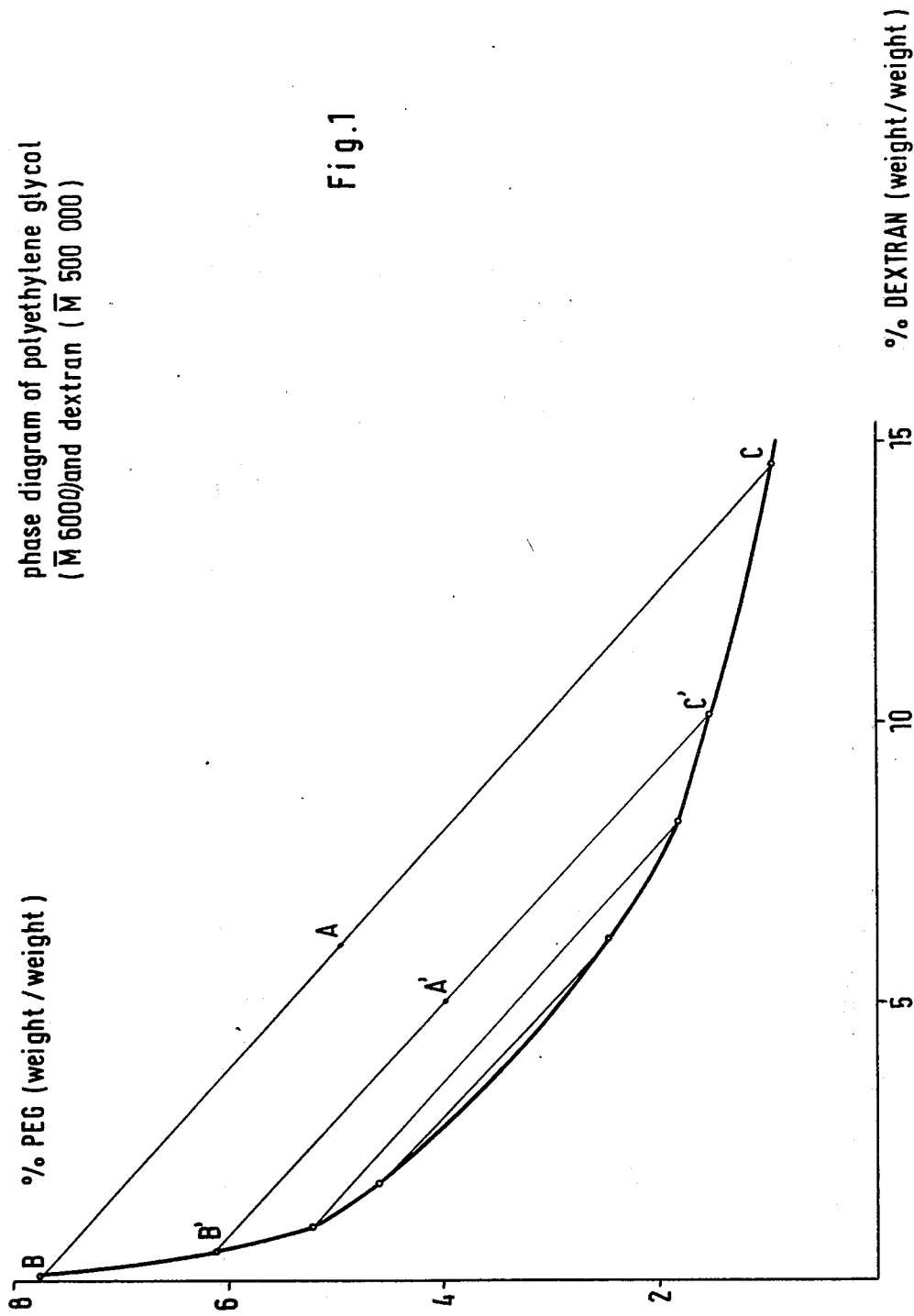
FIG. 1 is a phase-diagram of a system of polyethyleneglycol (mean molecular weight 6,000), dextran (mean molecular weight 500,000) and water.

FIG. 1 shows a phase-diagram for aqueous systems which contains dextran (mean molecular weight 500,000) and polyethyleneglycol (mean molecular weight 6000). Beneath the drawn line a phase separation does not appear so that this range means a homogenous system. Above the drawn line, however, a phase separation appears. Point A represents for example a system containing 6% by weight dextran and 5% by weight polyethyleneglycol. Such a system forms two phases; point B corresponds to the composition of the top phase and point C to the composition of the bottom phase. Each point lying on a line which connects the point B, A and C and which reflects the total composition of a particular system applies to a two-phase-system with the same composition of the two phases but different volumes of the phases. The proportion of the segment B–A to the segment A–C of the line which is defined by the points B and C and crosses the point A corresponds to the weight-proportion bottom-phase/top-phase. Since the density of the phases is about 1 g/ml the proportion of the segments B–A and A–C reflects approximately the proportion of the volumes of the two phases. (For further discussion of such a phase-diagram please compare Albertsson, Methods Microbiol. 5B, 385 to 423 (1971)).

Nernst's equation applies to these aqueous two-phase-systems too:

$$K = C_t/C_b,$$

where $C_t$ and $C_b$ have the meaning of the concentration in the top phase and in the bottom phase, respectively, of a substance which is partitioned over both phases. In addition the partition can be described in a general manner with the Bronsted-equation:

$$\ln K = \lambda M/k\,T,$$

where M has the meaning of the molecular weight and T the absolute temperature and lambda has the meaning of a factor which depends on other features of the system. It can be seen from the equation that very small changes of lambda at large molecular weight result in drastic absolute changes of the distribution-coefficient.

Even in the case that it was theoretically conceivable before the present invention to partition enzymes into one phase of a multi-phase system the additional problem had to be solved to partitione cell-fragments or cells (from which the enzymes were to be separated) in one phase too, i.e. in another phase. This problem has only been solved by the present invention.

In the following the process according to the invention will be explained in greater detail on the basis of the polyethyleneglycol/dextran-system, which has been selected as an example, for pullulanase and maltase as examples for enzymes. For this system it was found that the cells surprisingly go completely into the dextran-rich lower phase. For these enzymes distribution-coefficients of e.g. 0.3 can be found. This means that the proportion of the enzyme-concentration in the top-phase to the enzyme-concentration in the bottom phase is 0.3:1. Therefore a system with a K of 0.3 is suitable for a separation of enzymes in the top-phase, since the cells are completely present in the bottom phase. However, a volume proportion of the two phases must be used which is not optimal to achieve a satisfactory separation. This is clear from the following definition of the separation degree G:

$$G = C_t V_t/C_b V_b = K V_t/V_b,$$

wherein $V_t$ and $V_b$ have the meaning of the volume of the top-phase and the bottom-phase, respectively. From the foregoing equation for the separation degree it follows that in the case of a K-value of 0.3 the volume of the top-phase has to be about three times as great as that of the bottom phase in order to enrich 50% of a partioned enzyme in the top-phase.

Figure 13:
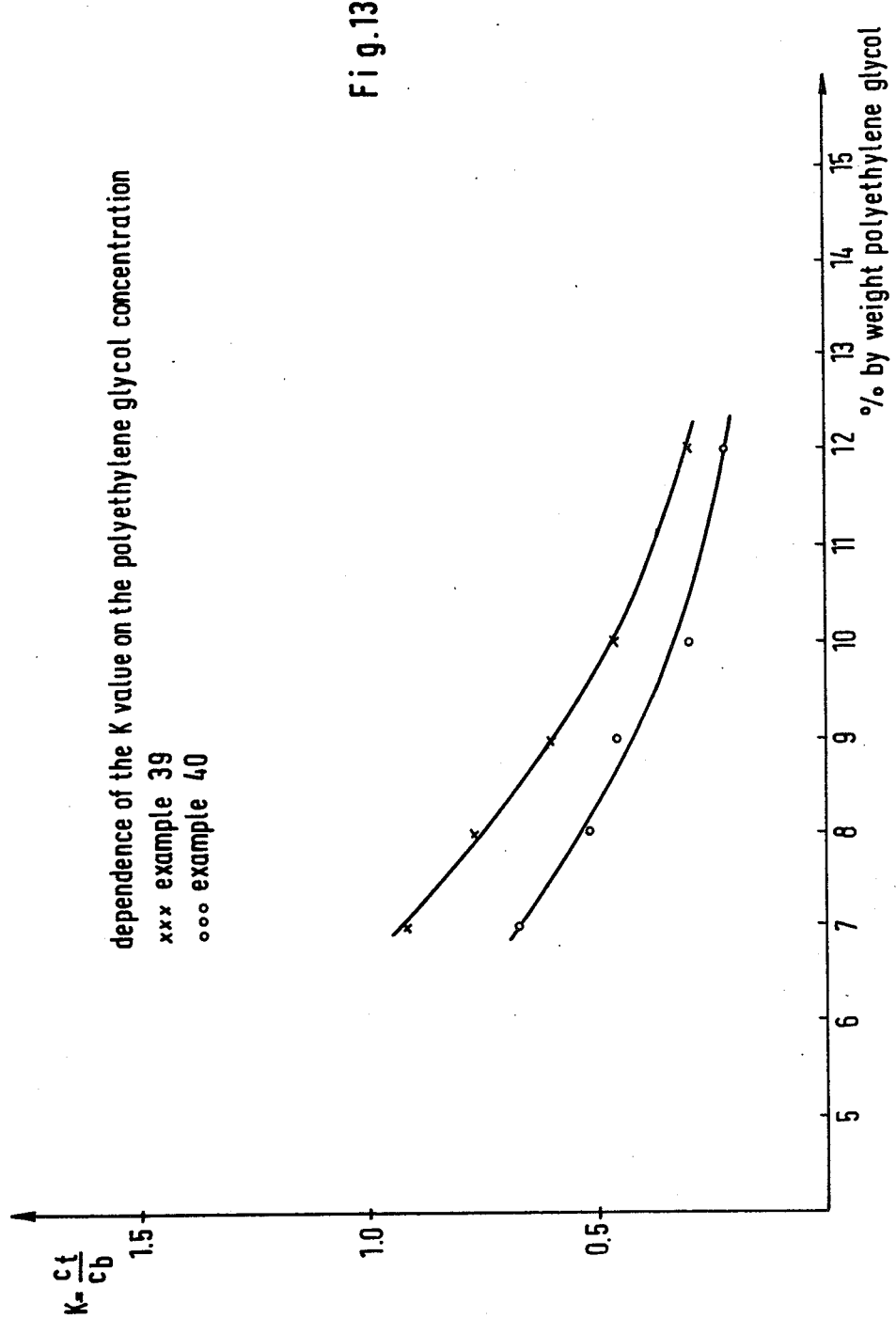
FIG. 13 shows the dependence of the distribution-coefficient K for maltase upon the concentration and the mean molecular weight of the polyethyleneglycol used in aqueous polyethyleneglycol/dextran-systems.

With respect to the separation-degree it is preferable therefore to use a multi-phase system having a total content of polyethyleneglycol of at least 1 and preferably 4 to 8% by weight and a total content of dextran of 0.1 to 15% by weight and preferably 0.1 to 7% by weight. For the same components of the system the distribution coefficient of the enzymes may in addition become more favourable if the polyethyleneglycol-concentration decreases (compare FIG. 13).

Figure 2:
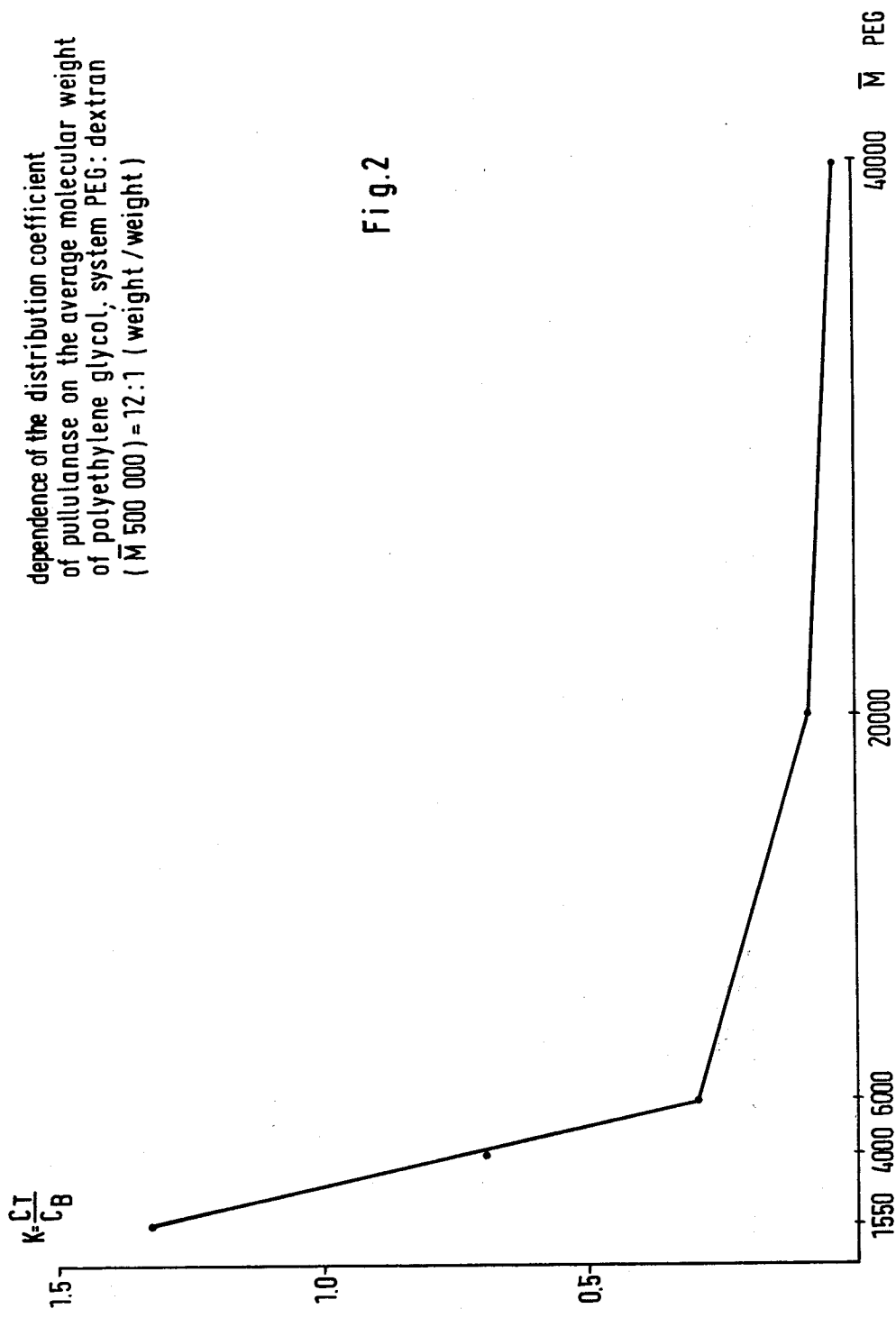
FIG. 2 shows the dependence of the distribution-coefficient K for pullulanase upon the mean molecular weight of polyethyleneglycol in an aqueous polyethyleneglycol/dextran-system.
Figure 3:
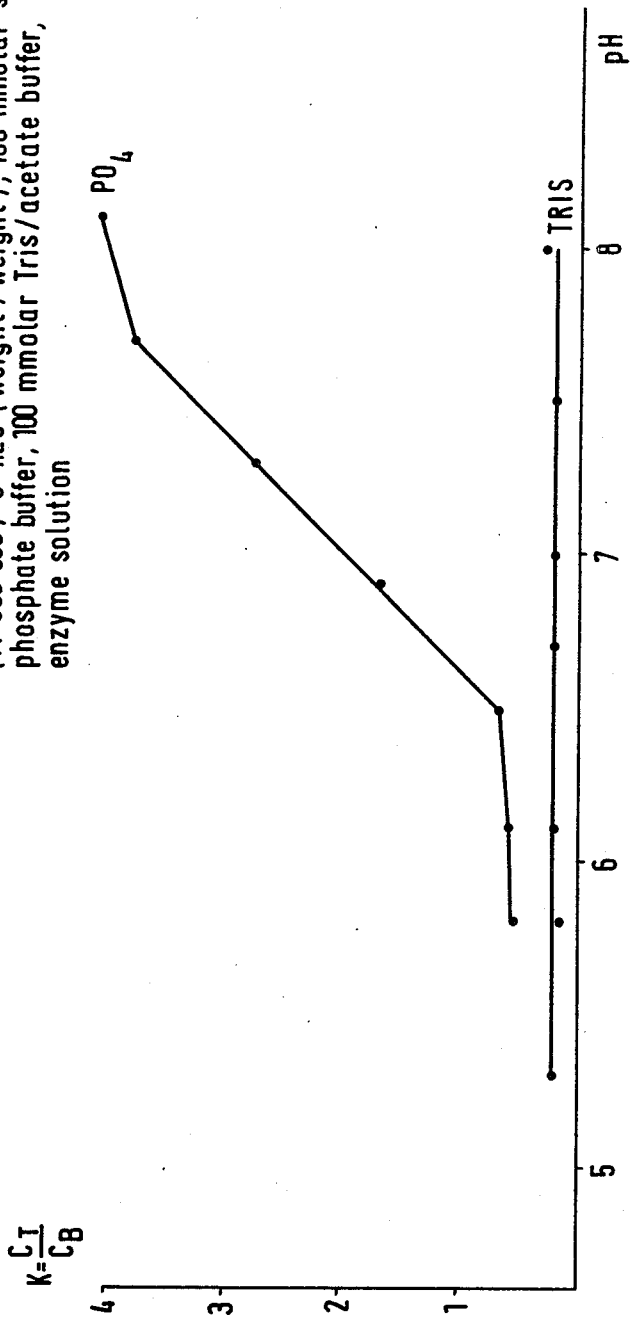
FIG. 3 shows the dependence of the distribution coefficient K for pullulanase upon the pH and buffer ion in an aqueous polyethyleneglycol/dextran-system.
Figure 4:
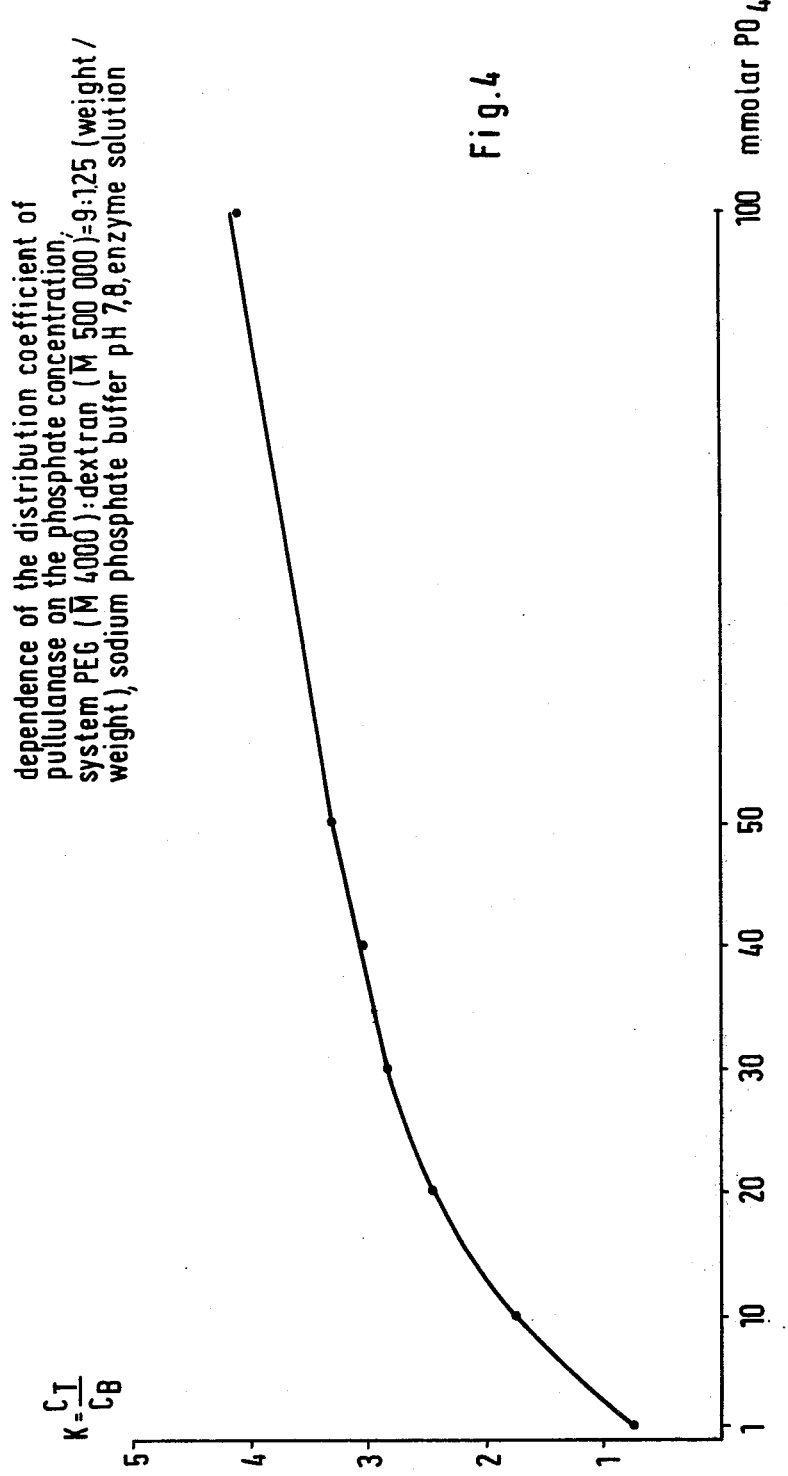
FIG. 4 shows the dependence of the distribution-coefficient K for pullulanase upon the phosphate concentration in an aqueous polyethyleneglycol/dextran-system.

Since it is desirable to use even higher K-values than 0.3 further parameters with which the distribution-coefficient of the enzymes can be shifted to higher values will be examined in the following. From FIGS. 2 and 13 it is clear that for the use of polyethyleneglycol with fairly short chains the distribution-coefficient increases rapidly and can reach values of about 1. (This stresses from another point of view, that according to the invention it as advantageous to use polyalcohols and polyethers having clearly smaller average molecular weights than that of pullanase preferably an average molecular weight of smaller than 40,000, more preferably smaller than 10,000, most preferably smaller than 6,000, e.g. in the range of 5,000 to 1,550, e.g. of about 4,000).

By the addition of phosphate ions, e.g. orthophosphate, pyrophosphate, polyphosphate and/or metaphosphate ions, particularly orthophosphate ions it is possible to increase the distribution coefficient as a function of the pH in a surprising manner (FIGS. 3 to 4 and 9 to 12).

Pullulanase

When the distribution of this enzyme is carried out in an aqueous polyethyleneglycol/dextran-system with a distribution-coefficient of 0.3 and with a 100-mmolar sodium phosphate-concentration and a volume-ratio of the top-phase to the bottom phase of 10:1, the following yield results from a single partition step:

$$\text{yield (\%)} = 100/(1 + V_b/V_t K) = 97.$$

It is preferable to use a phosphate ion-concentration of more than 0.001, more preferably more than 0.02 m and at a pH-value of 6–9 and in particular 7 to 8.

It is surprising for the following reasons that the process according to the invention can be carried out in a particularly useful manner in the presence of phosphate ions and at a pH of about 7.

1. When the pH is varied in the range of 6 to 8 without adding phosphate ions it is not possible to influence the distribution coefficient noticeably. In addition, an increase in the ionic strength, for example with sodium-chloride, leads to a decrease of the distribution coefficient so that with a high sodium-chloride-concentration the dextranrich bottom-phase is preferred (comp. also FIG. 10).

2. Pullulanase shows a maximum activity at pH 5. Since, however, it is possible to carry out the process according to the invention at higher pH-values without any damage to the pullulanase activity it is assumed that the high-molecular weight compounds stabilize the enzyme. These considerations apply accordingly to other enzymes.

In addition the phase-diagram and the distribution-coefficient depend on the temperature. Since pullulanase can be stabilized by the high-molecular weight compounds, e.g. polyethyleneglycol and dextran, it is possible to work at room temperature without any activity loss. These considerations apply accordingly to other enzymes too.

A preferred method for the separation of pullulanase from high-molecular weight compounds and proteins consists in the precipitation of pullulanase with a compound of the following general formula:

$NR^1R^2R^3R^4X$, wherein $R^1$ is an organic group having at least 10 carbon-atoms, $R^2$, $R^3$ and $R^4$, which may be the same or different, are hydrogen atoms or organic groups having 1 to 20 carbon-atoms, where the organic groups for $R^1$ to $R^4$ may be selected from the group consisting of alcyl, substituted alcyl, alcenyl, aryl, substituted aryl, aralcyl and saturated and unsaturated cyclic groups, where $R^3$ and $R^4$ can form together a cyclic group, where $R^2$ may be absent, if it is unsaturated cyclic group, and where X is an inorganic or organic anion, e.g. a haloid, phosphate, nitrate, sulfate or acetate ion.

Examples for the amoniumcation are dodecylmethylammonium, dodecyltrimethylammonium, tetradecylammonium, cetylmethylammonium, cetyldimethylammonium, cetyltrimethylammonium, octadecyltrimethylammonium, benzyldodecyldimethylammonium, N,N-diethylmorpholinium, cetylpyridinium, decenyltrihydroxyethylammonium, dioctadecyldiethylammonium, dioctadecylmorpholinium, dilauryldimethylammonium and distearyl-2-chloroethylbutylammonium ion.

Of course, it is possible to precipitate the pullulanase after the separation of the high-molecular weight compounds and the proteins. It is clear that the pullulanase precipitation is applicable to other processes where pullulanase appears or is used then the process according to the invention.

Surprisingly it is possible to precipitate the pullulanase in the form of a stoichiometric compound with the empirical formula pullulanase . ammoniumcation and its salts, respectively, with the empirical formula pullulanase . $R_4NX$. It is possible to dissolve this precipitate in salt-solutions having increasing ion-strength, as can be drawn from the following examples.

From the German Patent Application No. 2,251,855 it is, however, already known, that enzymes, e.g. pullulanase, have been treated with long chain quaternary ammonium-compounds to improve their storage stability. According to the passage from the bottom of page 4 to the top of page 5 of this quotation the treated enzymes ought to be present in a solubilized form (example 3) or intracellularly (example 1) or on inert carriers (examples 2 and 4). Therefore this prior art does not give any evidence of a stiochiometric precipitation of pullulanase. Stoichiometric precipitations of enzymes by long-chain ammonium-compounds have not become known up to now. The formation of a stoichiometric compound for pullulanase is even more surprising as for example α-amylases and proteases remain in solution if, for example, pullulanase is precipitated by cetyltrimethylammonium bromide.

The specific precipitation of pullulanase offers the advantage that interfering activities such as amylase, glucosidase and proteases can be separated.

The percipitates formed can be easily centrifuged off at small g-numbers.

Pullulanase splits glucose-α-1-6-bonds and is together with other enzymes used to debranch and completely decompose starches and glycogenes, for example in breweries, in the production of bread and in analytical chemistry. Pure pullulanase can be used for the linearisation of starch and to recover linear oligo or polyglucanes-α-1-4.

The following examples for pullulanase explain that it is already possible to form with only one singular high-molecular weight compound from the group consisting of unsubstituted or substituted polyalcohols, polyethers, polyesters and polysaccharides and an inorganic salt an aqueous multi-phase system; it is for example possible to work in the presence of polyethyleneglycol and ammonium-sulfate and, if desired, phosphate.

Maltase

All aspects correspond substantially to those of pullulanase the effects, however, being rather less clear. For the embodiment of the process according to the invention with at least two high-molecular weight compounds the following applies: if the process is carried out in the presence of phosphate ions it is possible to use a phosphate ion-concentration of more than 0.1, preferably more than 0.3 and more preferably more than 0.5 m.

Aminoacyl-tRNA-synthetases

The following examples for aminoacyl-tRNA-synthetases explain that it is already possible to form an aqueous multi-phase system with one single high-molecular weight compound from the group consisting of unsubstituted or substituted polyalcohols, polyethers, polyesters and polysaccharides and cells and cell-fragments, respectively, as additional "high-molecular weight-compounds"; it is for example possible to work in the presence of polyethyleneglycol and preferably in the presence of potassium phosphate.

In the following the invention is explained by examples in more detail.

 $\overline{M}$ means average molecular weight.

EXAMPLE 1 (FIG. 1)

This example for a phase diagram for aqueous systems containing polyethylene glycol ($\overline{M}$ 6,000) and dextran ($\overline{M}$ 500,000) is based on the data of Albertsson.

EXAMPLE 2 (FIG. 2)

The distribution coefficient K of pullulanase was examined as a function of the mean molecular weight of polyethylene glycol in an aqueous system containing polyethylene glycol, dextran ($\overline{M}$ 500,000) and enzyme. The ratio of polyethylene glycol to dextran was 12:1 (weight basis). The resulting data are graphically plotted in FIG. 2.

EXAMPLE 3

The distribution coefficient K of pullulanase was examined as a function of the mean molecular weight of dextran in an aqueous system containing polyethylene glycol ($\overline{M}$ 4,000), dextran, enzyme and
(a) without any phosphate and
(b) with phosphate (concentration 0.1 m, pH 7.5) respectively. The activity of the used enzyme solution was 20.8 U/ml, a salt concentration 0.02 m and a pH 7.5.

Each system contained 10 parts polyethylene glycol and 5 parts dextran and was completed to 100 parts by adding water.

The resulting data are listed in table 1. From these data it is clear that the mean molecular weight of the dextran used hardly influences the distribution coefficient K.

Table 1

| $\overline{M}$ dextran × 10$^5$ | volume top phase (ml) | volume bottom phase (ml) | U/ml top phase | U/ml bottom phase | K value |
| --- | --- | --- | --- | --- | --- |
| a) | | | | | |
| 1.1 | 7.7 | 1.9 | 6.4 | 28.8 | 0.22 |
| 5.0 | 7.8 | 2.0 | 7.0 | 24.8 | 0.28 |
| 20.0 | 7.8 | 1.8 | 6.8 | 28.4 | 0.24 |
| 10.0+ | 8.0 | 1.8 | 7.9 | 22.7 | 0.35 |
| b) | | | | | |
| 1.1 | 7.5 | 2.0 | 4.5 | 3.9 | 1.15 |
| 5.0 | 7.4 | 2.1 | 4.6 | 3.6 | 1.28 |
| 20.0 | 7.6 | 2.0 | 4.5 | 3.7 | 1.22 |
| 10.0+ | 7.8 | 1.6 | 4.3 | 5.1 | 0.80 |

+sodium dextransulfate

EXAMPLE 4 (FIG. 3)

The distribution coefficient K of pullulanase was examined as a function of the pH and of the buffer ions in an aqueous system containing polyethylene glycol ($\overline{M}$ 4,000), dextran ($\overline{M}$ 500,000), enzyme and
(a) sodium phosphate
(b) Tris/acetate.
The ratio of polyethylene glycol to dextran was 9:1.25 (weight basis) and the concentration of the buffers (a) and (b) 100 m molar in each case. The resulting data are graphically plotted in FIG. 3.

EXAMPLE 5 (FIG. 4)

The partition coefficient K of pullulanase was examined as a function of the phosphate concentration in an aqueous system containing polyethylene glycol ($\overline{M}$ 4,000), dextran (M 500,000), enzyme and sodium phosphate. The ratio of polyethylene glycol to dextran was 9:1.25 (weight basis). The pH of the sodium phosphate buffer was 7.8. The resulting data are graphically plotted in FIG. 4.

EXAMPLE 6 (FIG. 5)

Figure 5:
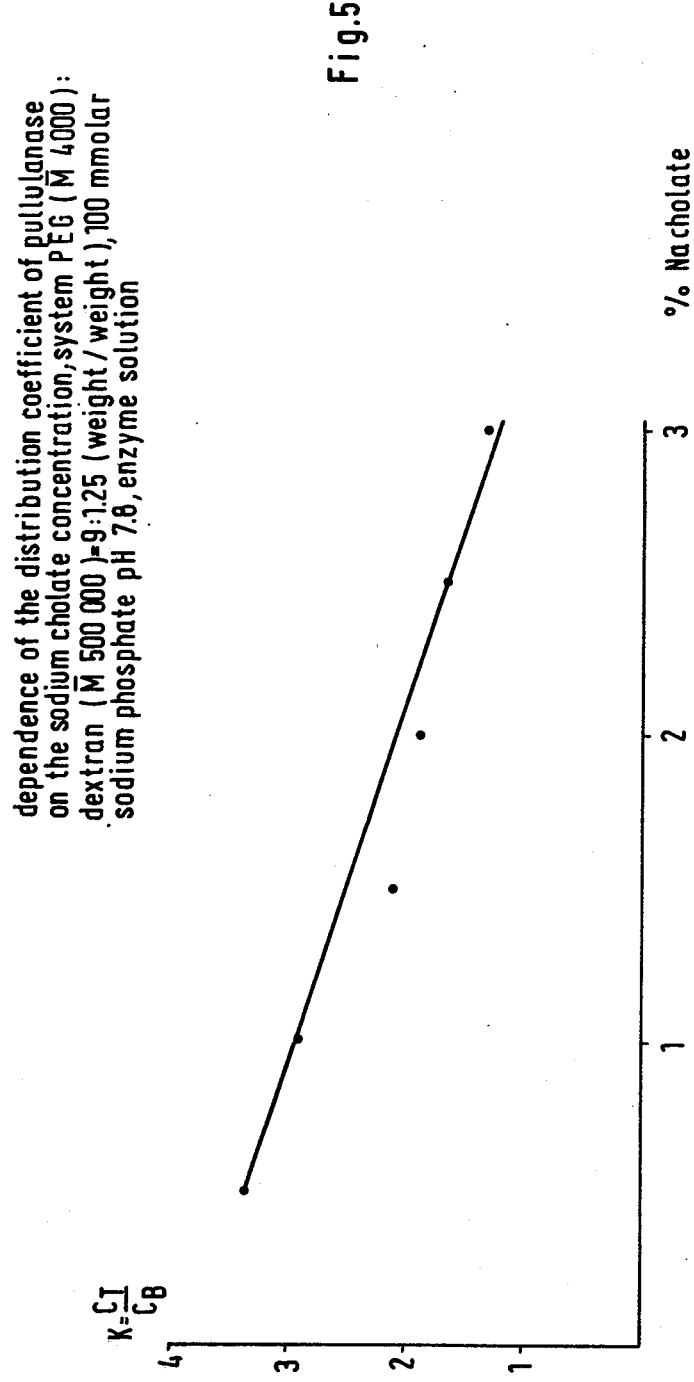
FIG. 5 shows the dependence of the distribution-coefficient K for pullulanase upon the sodium cholate-concentration in an aqueous polyethyleneglycol/dextran-system.

The distribution coefficient K of pullulanase was examined as a function of the sodium cholate concentration in an aqueous system containing polyethylene glycol ($\overline{M}$ 4,000), dextran ($\overline{M}$ 500,000), sodium phosphate and enzyme. The ratio of polyethylene glycol to dextran was 9:1.25 (weight basis); the concentration of sodium phosphate was 100 mmolar and its pH was 7.8. The resulting data are graphically plotted in FIG. 5.

EXAMPLE 7 (FIG. 6)

Figure 6:
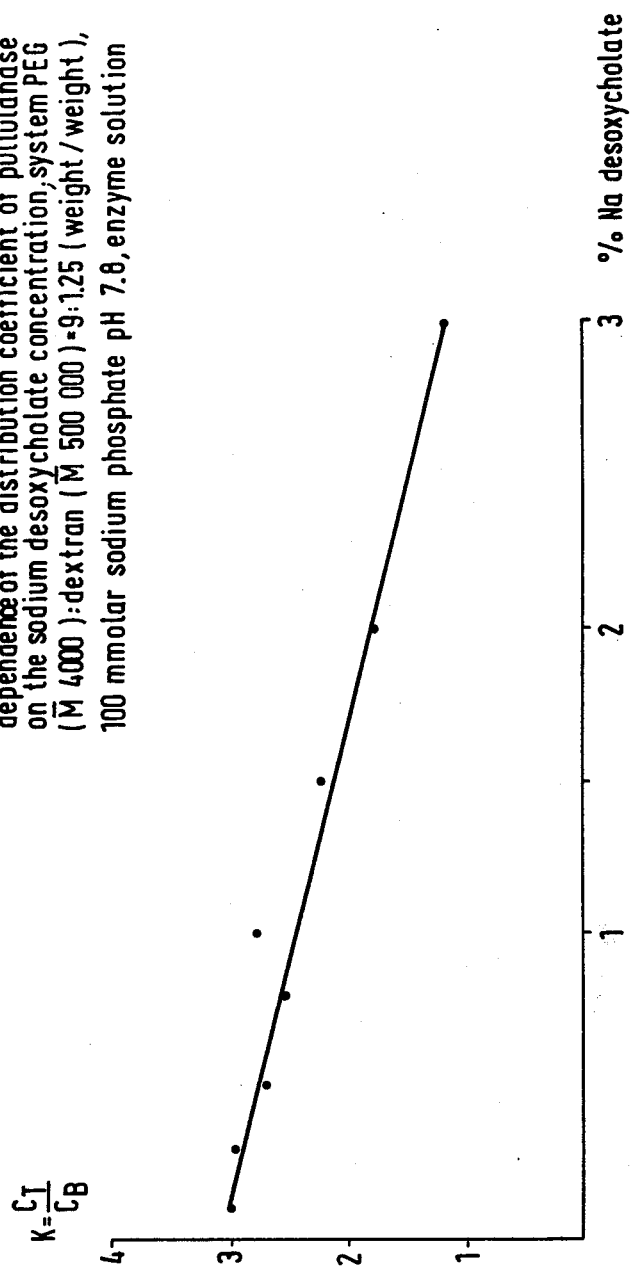
FIG. 6 shows the dependence of the distribution-coefficient K for pullulanase upon the sodium desoxycholate-concentration in an aqueous polyethyleneglycol/dextran-system.

The distribution coefficient K of pullulanase was examined as a function of the sodiumdesoxycholate concentration in an aqueous system containing polyethylene glycol ($\overline{M}$ 4,000), dextran ($\overline{M}$ 500,000), sodium phosphate and enzyme. The ratio of polyethylene glycol to dextran was 9:1.25 (weight basis); the concentration of sodium phosphate was 100 mmolar and its pH was 7.8. The resulting data are graphically plotted in FIG. 6.

EXAMPLE 8 (FIG. 7)

Figure 7:
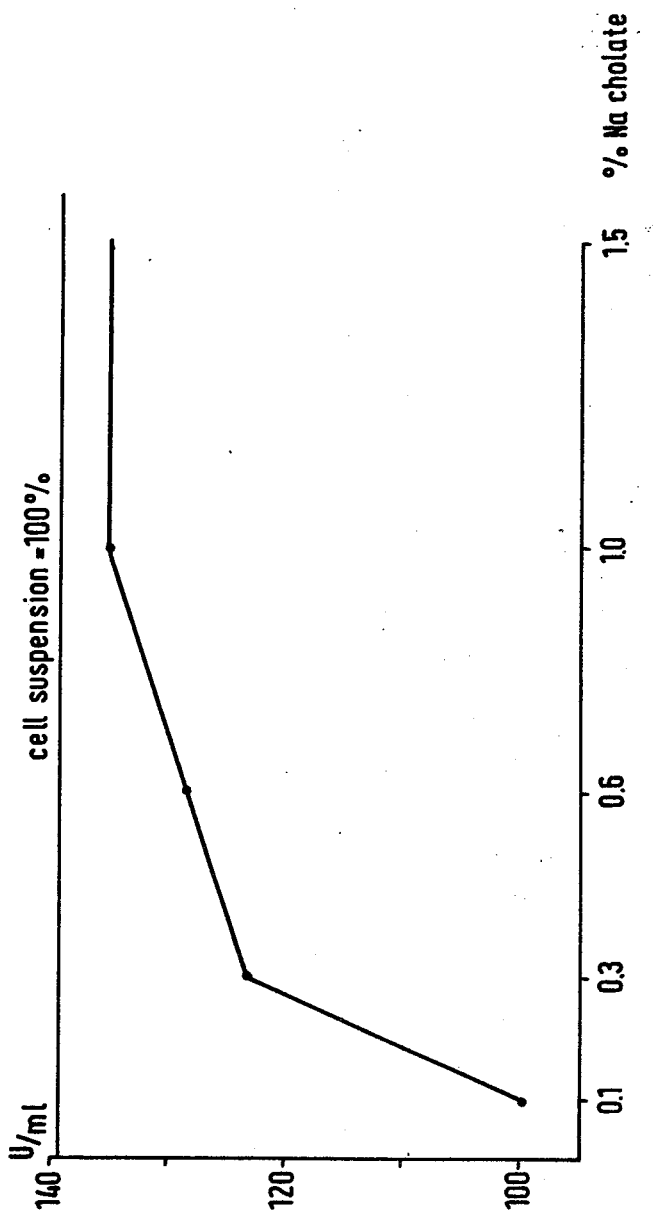
FIG. 7 shows the degree of separation of pullulanase from Klebsiella-cells in the top phase as a function of the sodium-cholate-concentration in an aqueous polyethyleneglycol/dextran-system.

The separability of pullulanase from K. pneumoniae cells from which the enzyme had been dissolved in the top phase of an aqueous system containing polyethylene glycol ($\overline{M}$ 4,000), dextran ($\overline{M}$ 500,000), sodium phosphate and cells was examined as a function of the sodium cholate concentration. The ratio of polyethylene glycol to dextran was 9:1.25 (weight basis) and the ratio of cells to the buffer was 1:1.4; the concentration of sodium phosphate was 200 mmolar and its pH was 8.0. The resulting data are graphically plotted in FIG. 7.

EXAMPLE 9 (FIG. 8)

Figure 8:
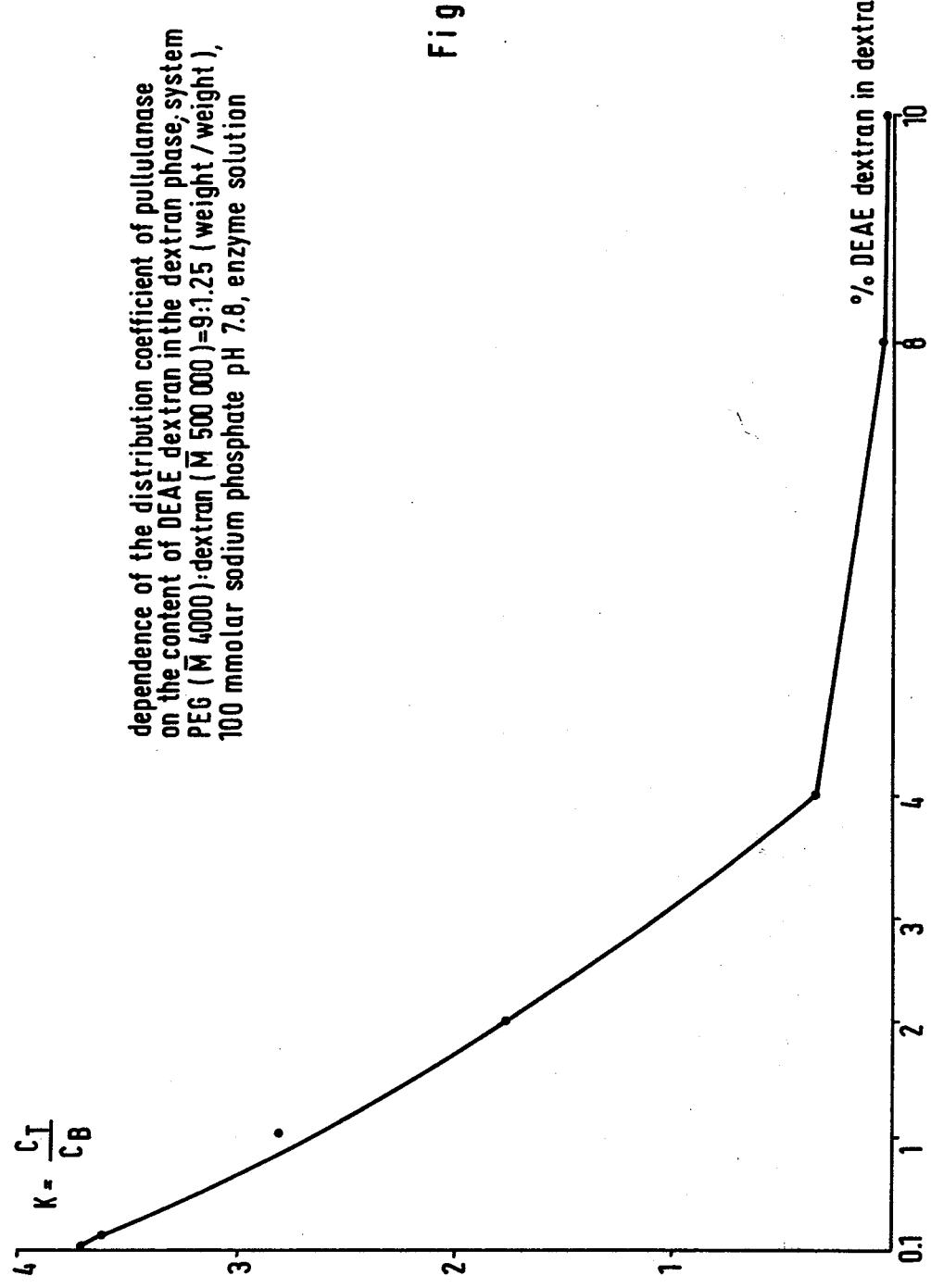
FIG. 8 shows the dependence of the distribution-coefficient K for pullulanase upon the content of DEAE-dextran in the bottom phase of an aqueous polyethyleneglycol/dextran-system.
Figure 9:
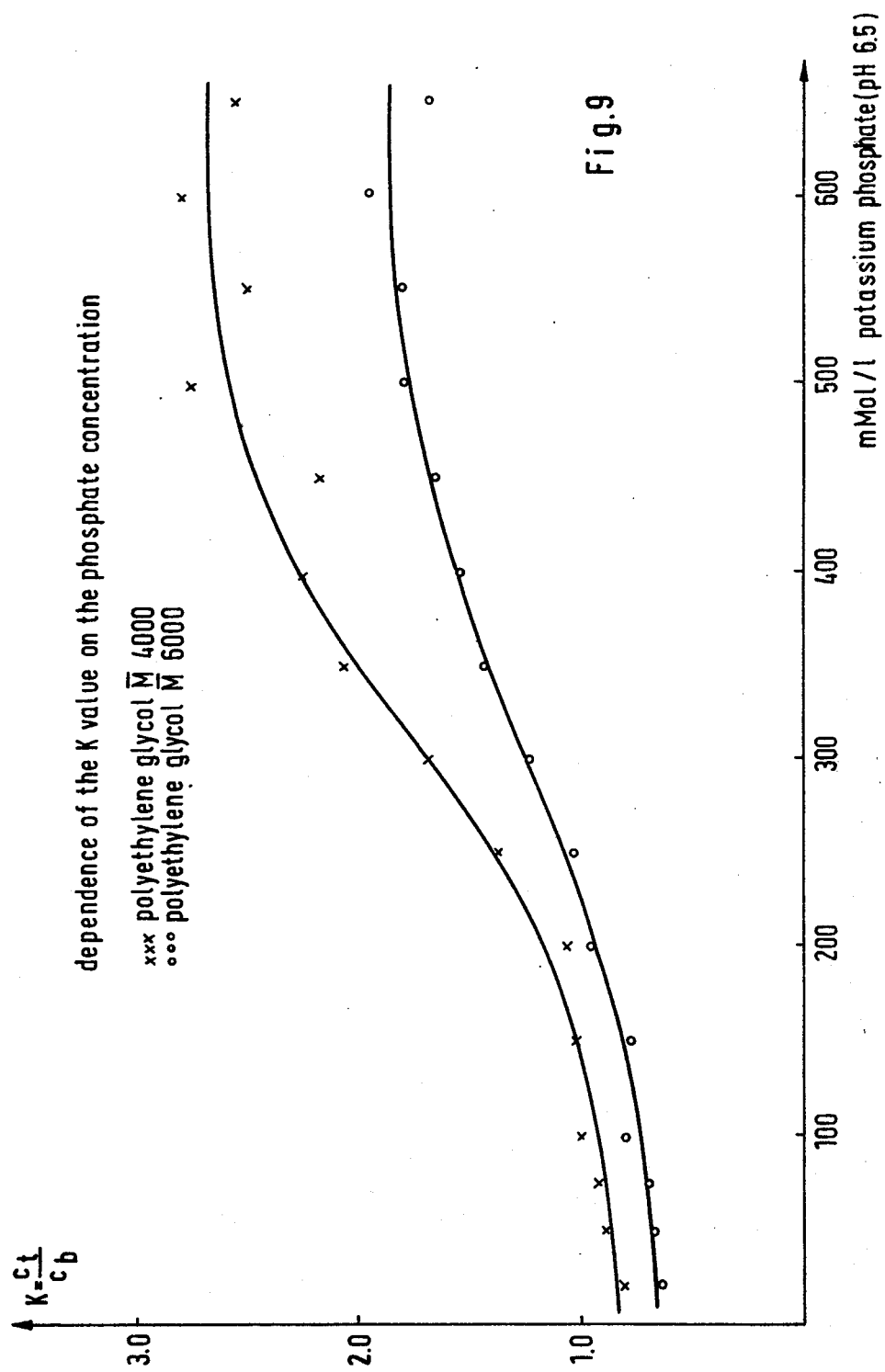
FIG. 9 shows the dependence of the distribution-coefficient K for maltase upon the phosphate-concentration in an aqueous polyethyleneglycol/dextran-system.
Figure 10:
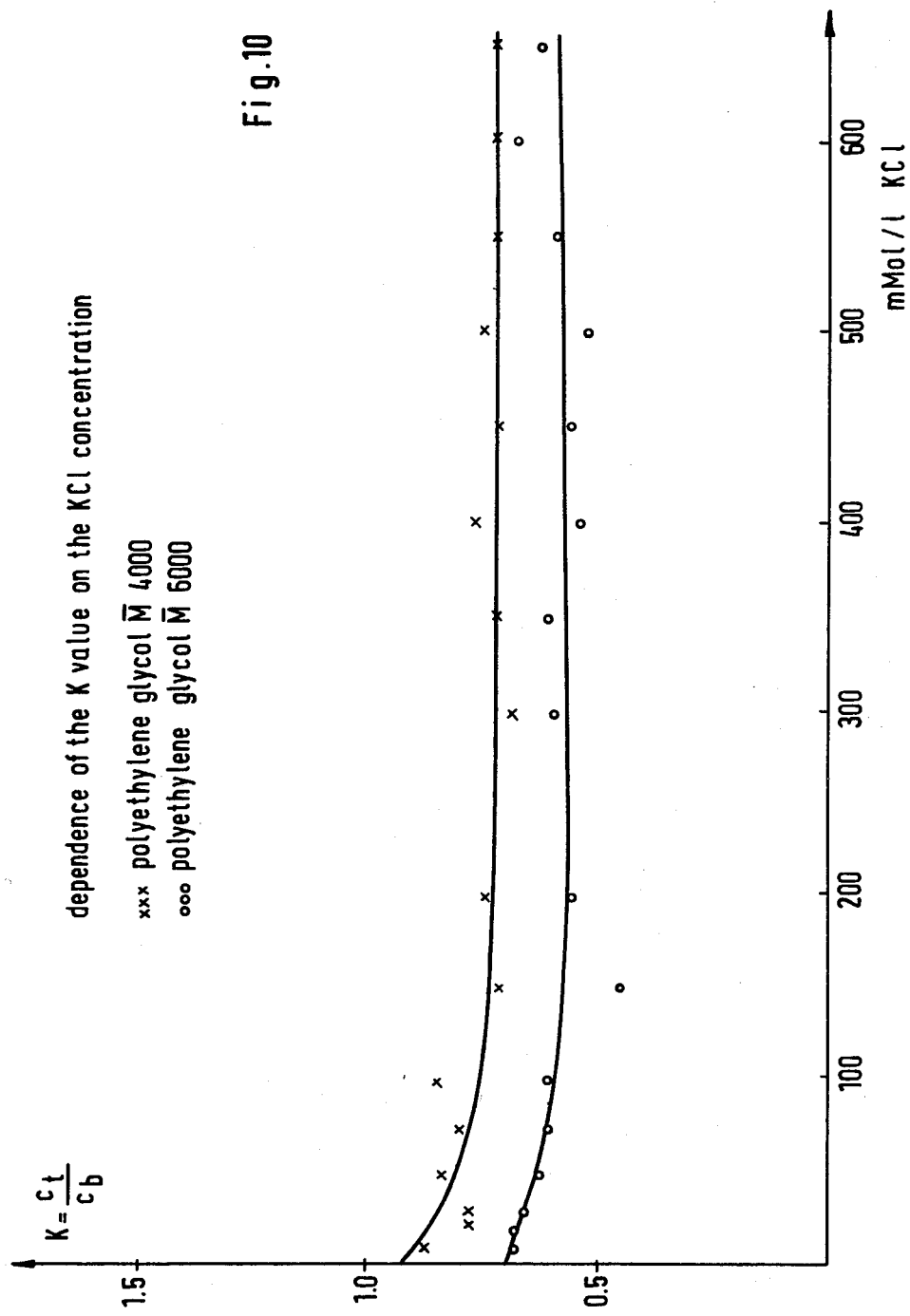
FIG. 10 shows the dependence of the distribution-coefficient K for maltase upon the potassium chloride-concentration in aqueous polyethyleneglycol/dextran systems.
Figure 11:
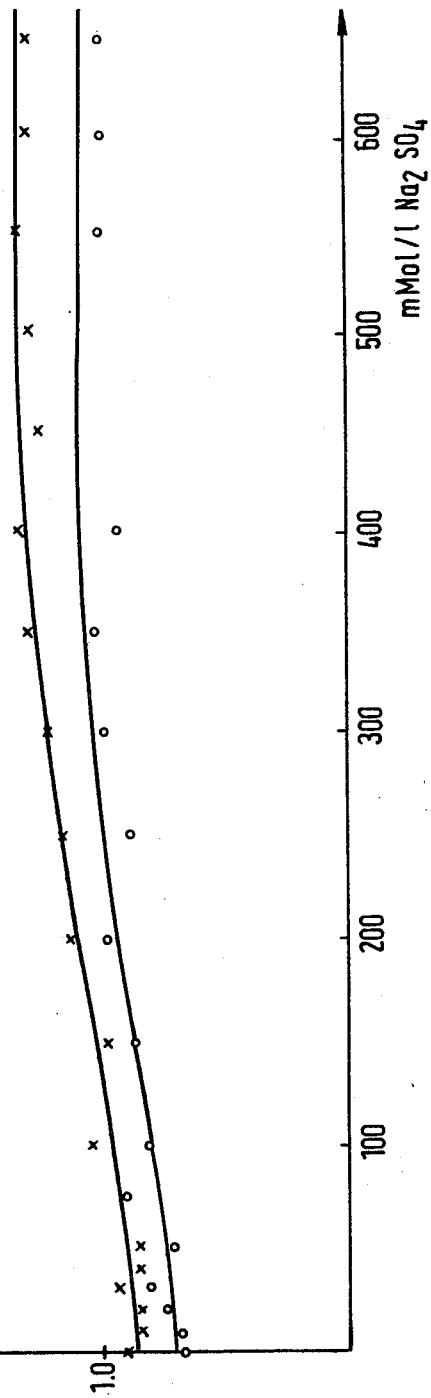
FIG. 11 shows the dependence of the distribution-coefficient K for maltase upon the sodium sulfate-concentration in aqueous polyethyleneglycol/dextran-systems.
Figure 12:
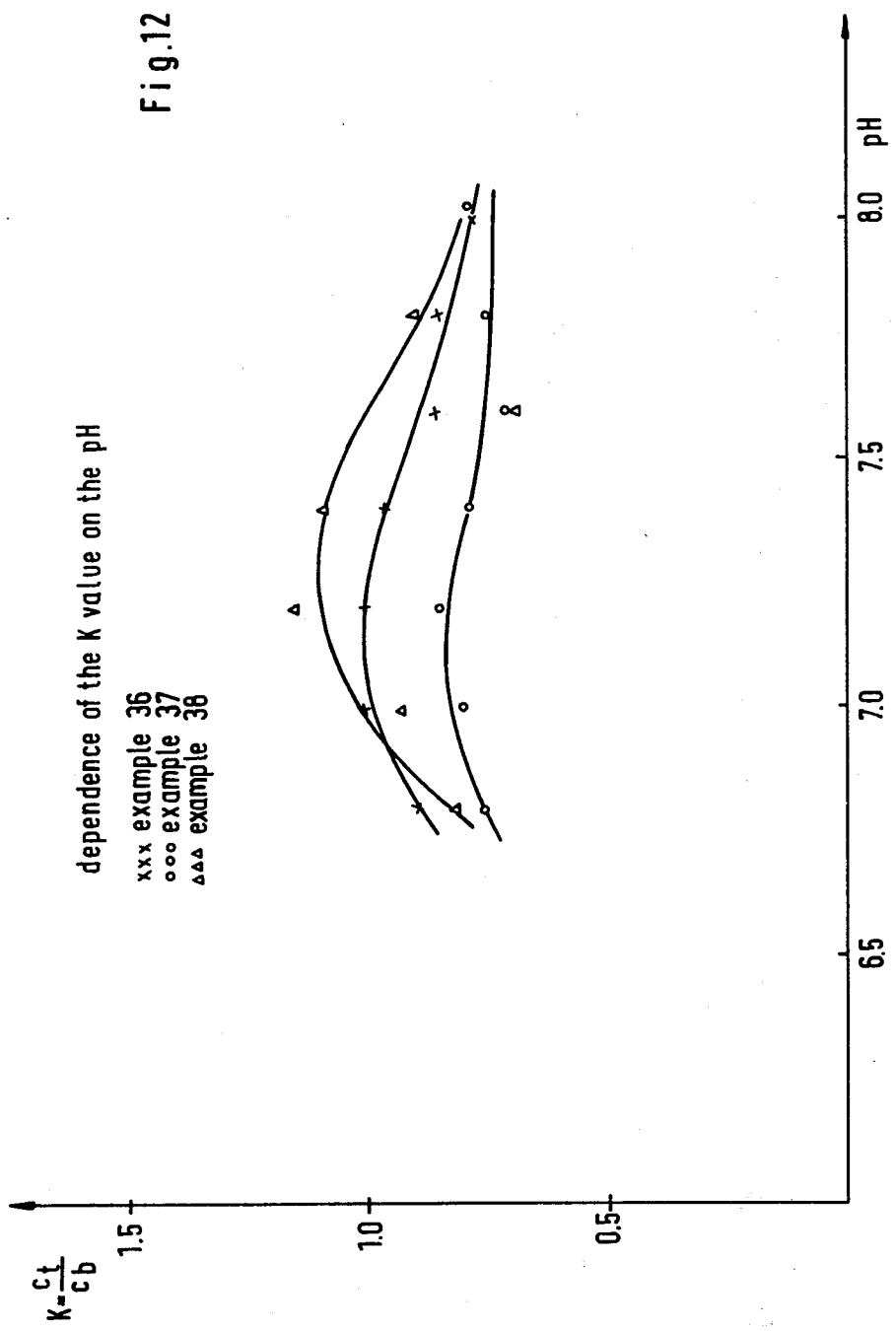
FIG. 12 shows the dependence of the distribution-coefficient K for maltase upon the pH in aqueous polyethyleneglycol/dextran-systems.

The distribution coefficient K of pullulanase in an aqueous system containing polyethylene glycol ($\overline{M}$ 4,000), dextran ($\overline{M}$ 500,000), sodium phosphate and enzyme was examined as a function of the content of DEAE-dextran in the dextran phase. The ratio of polyethylene glycol to dextran was 9:1.25 (weight basis); the concentration of sodium phosphate was 100 mmolar and its pH was 7.8. The resulting data are graphically plotted in FIG. 8.

EXAMPLE 10

The pullulanase yield of a one step extraction in an aqueous system containing polyethylene glycol ($\overline{M}$ 4,000), dextran ($\overline{M}$, 500,000), sodium phosphate and enzyme was examined as a function of the phosphate concentration. The ratio of polyethylene glycol to dextran was 9:1.25 (weight basis) and the pH of sodium phosphate was 7.8. The total volume of the used system was 5 ml and the activity of the used enzyme solution corresponded to 231.4 U altogether. The results are summarized in the following table 2.

Table 2

| sample No. | phosphate concentration (mmolar) | total activity found (U) | top phase vol. (ml) | top phase activity (U/ml) | top phase activity (total U) | bottom phase vol. (ml) | bottom phase activity (U/ml) | bottom phase activity (total U) | $K = \frac{C_t}{C_b}$ | Yield (%) |
| --- | --- | --- | --- | --- | --- | --- | --- | --- | --- | --- |
| 1 | 1 | 224.4 | 4.5 | 45.7 | 205.7 | 0.5 | 37.4 | 18.7 | 1.22 | 91.7 |
| 2 | 10 | 229.5 | 4.5 | 47.5 | 213.9 | 0.5 | 31.2 | 15.6 | 1.52 | 93.2 |
| 3 | 20 | 252.9 | 4.5 | 52.7 | 237.2 | 0.5 | 31.4 | 15.7 | 1.67 | 93.8 |
| 4 | 30 | 261.1 | 4.5 | 55.1 | 248.0 | 0.5 | 26.1 | 13.1 | 2.11 | 95.0 |
| 5 | 40 | 232.4 | 4.6 | 48.2 | 221.7 | 0.4 | 26.9 | 10.7 | 1.79 | 95.4 |
| 6 | 50 | 239.7 | 4.6 | 50.2 | 230.9 | 0.4 | 22.0 | 8.8 | 2.28 | 96.3 |
| 7 | 100 | 232.5 | 4.6 | 49.4 | 227.2 | 0.4 | 13.3 | 5.3 | 3.70 | 97.7 |
| 8 | 200 | 255.6 | 4.5 | 55.5 | 249.8 | 0.5 | 11.6 | 5.8 | 4.78 | 97.7 |

Table 2-continued

| sample No. | phosphate concentration (mmolar) | total activity found (U) | top phase | | | bottom phase | | | $K = \dfrac{C_t}{C_b}$ | Yield (%) |
|---|---|---|---|---|---|---|---|---|---|---|
| | | | vol. (ml) | activity (U/ml) | activity (total U) | vol. (ml) | activity (U/ml) | activity (total U) | | |
| 9 | 300 | 261.6 | 4.4 | 58.4 | 256.9 | 0.6 | 7.9 | 4.7 | 7.39 | 98.2 |

EXAMPLE 11

*Klebsiella pneumoniae* cells were suspended with the 1.4 fold volume of an aqueous 0.5 m sodium phosphate buffer (pH 8.0). 1% sodium cholate was added; the suspension was vigorously stirred for 90 minutes at room temperature. Then 9% polyethylene glycol ($\overline{M}$ 4,000) and 1.25% dextran ($\overline{M}$ 500,000) were weighed, added and mixed with a mixer (vibro-mixer) for about 10 minutes; the suspension was centrifuged at 12,000 Upm for 20 minutes. The cell-free super natent upper phase could easily be poured off. Dialysis was carried out against running water for 48 hours (cooling room).

EXAMPLES 12 TO 14

These examples are to explain that with respect to the recovery of pullulanase from a polyethylene glycol-rich phase different ways may be selected.

(EXAMPLE 12)

Eighteen percent ammonium sulfate was added to a polyethylene glycol-rich phase containing pullulanase (example 11) so that a new two phase system polyethylene glycol/ammonium sulfate was formed. The pullulanase went quantatively into the salt phase. It was possible to separate the absolutely clear phases in a separator. The enzyme was precipitated from the bottom phase by increasing the ammonium sulfate concentration to 35 %. The precipitate was centrifuged, dissolved in a 20 mmolar phosphate buffer and dialysed against the same buffer. The pullulanase obtained in this manner had a specific activity of 28 U/mg and was according to the results of the electrophoresis about 70% pure. The yield was 78%. The preparation contained traces of protease.

(EXAMPLE 13)

By dialysis against water of a top phase according to example 11 the detergents were removed and the salt concentration in the solution was increased to a level of about 0.1 m (phosphate); the enzyme was bound to DEAE cellulose. The DEAE cellulose was easily filtered off or separated in a basket centrifuge. The polyethylene glycol was nearly completely removed by washing the DEAE cellulose with buffer. Then the pullulanase was elutriated with a buffer having sufficient salt concentration. This procedure was also applicable on a technical scale. The yields were 30 to 50%.

(EXAMPLE 14)

A new two-phased system was formed by adding dextran containing about 8% DEAE dextran to a polyethylene glycol-rich phase. For this DEAE dextran content of about 8% the distribution coefficient K is smaller than 0.05, so that nearly all of the enzyme was transferred to the bottom phase (cf FIG. 8). In this way concentrating was possible by adjusting the volumes properly.

EXAMPLE 15

A system according to Albertsson, Biochemistry 12, 2525 (1973) was used. The system contained 6.7% dextran ($\overline{M}$ 500,000), 8.0% ficoll and 5.3% polyethylene glycol ($\overline{M}$ 6,000) and was a two-phase system. A pullulanase solution having an activity of 20.8 U/ml, a salt concentration of 0.02 m and a pH of 7.5 was used.

The distribution coefficient was 0.66.

EXAMPLE 16

A system according to Albertsson, Biochemistry 12, 2525 (1973), containing 5% dextran ($\overline{M}$ 500,000), 6% ficoll, 4% polyethylene glycol ($\overline{M}$ 6,000) and 25% polypropylene glycol ($\overline{M}$ 2020) was used, and a three-phase system formed. A pullulanase solution having an activity of 20.8 U/ml, a salt concentration of 0.02 m and a pH of 7.5 was used.

The pullulanase was distributed as follows:
top phase: 1.3 U/ml;
middle phase: 5.2 U/ml;
bottom phase: 16.2 U/ml.
The following distribution coefficients result:

$$K_1 = C_t/C_{middle} + C_b = 0.06$$

$$K_2 = C_{middle}/C_t + C_b = 0.30$$

$$K_3 = C_b/C_t + C_{middle} = 2.49$$

$$K_4 = C_t/C_{middle} = 0.25$$

$$K_5 = C_{middle}/C_b = 0.32$$

EXAMPLE 17 (Comparative Example)

A system according Albertsson, Biochemistry 12, 2525, particularly 2527 right (1973), was used. For this reason 20 g *Klebsiella pneumoniae* cells was stirred in 150 ml (instead of 1,500 ml) having concentrations of 1% (weight/volume) Triton X-100, 2m sodium rhodanide, 1 mmolar EDTA and 10 mmolar tris (pH 8.0) for one hour at room temperature. 22.2 g dextran ($\overline{M}$ 500,000) and 17.8 g polyethylene glycol (M 6,000) were added to the suspension.

A clear separation into two phases took place. The cells were in the bottom phase. The test for the pullulanase activity was, however, remarkably disturbed by the sodium rhodanide present. (The use of sodium chloride which has been recommended as a substitute for sodium rhodanide (l.c. page 2526 right) is not satisfactory since small distribution coefficients result.)

EXAMPLE 18 (Determination of the Best CTAB Concentration)

In preceding experiments a decrease in the pullulanase yield in the precipitate of the CTAB precipitation had been recognized for greater CTAB concentrations. With respect to a dependence of the precipitation on the Mol ratio CTAB/pullulanase in the following the CTAB concentration in the precipitation recipe is given as μMol/U pullulanase.

The experiments were carried out in the following manner. Increasing amounts of a 10% CTAB solution were added to each 10 ml pullulanase solution (purity 60 to 70%, 0.02 to 0.03 m $PO_4^{---}$, pH 7.0, 38 U/ml) which was stirred for 15 minutes at 0 degrees centigrade. The precipitate was centrifuged off and dissolved in 0.5m potassium phosphate (pH 7.5). The results are listed in the following table 3.

Table 3

| μMol CTAB/U pullulanase | activity yield (%) |
|---|---|
| 0.12 | 70 |
| 0.14 | 72 |
| 0.16 | 82 |
| 0.18 | 80 |
| 0.24 | 72 |
| 0.32 | 60 |

EXAMPLE 19 (Dependence of the CTAB Precipitation on the Pullulanase Concentration)

The experiments were carried out in the following manner. A pullulanase solution (purity about 70%; 42 U/ml, 0.02 m $PO_4^{3-}$, pH 7.5) was diluted with increasing amounts of 0.02 m potassium phosphate solution (pH 7.5). The precipitation was affected by the addition of a 10% CTAB solution at a Mol ratio of 0.16 μMol/U. The system was stirred for 15 minutes at 0 degrees centigrade. The precipitates were centrifuged off and dissolved in 0.5 m potassium phosphate (pH 7.5). The results are listed in the following table 4.

Table 4

| μMol CTAB/U | V/ml | activity yield in the precipitate |
|---|---|---|
| 0.16 | 42.0 | 82% |
| 0.16 | 30.0 | 79% |
| 0.16 | 21.2 | 81% |
| 0.16 | 14.0 | 54% |
| 0.16 | 9.9 | 40% |

EXAMPLE 20 (Dependence of the CTAB Precipitation on the pH Value)

In each case 5 ml of a 60 to 70% pure pullulanase solution (42 U/ml, 0.02 to 0.03 m potassium phosphate, pH 7.5) were brought with 0.1 m hydrochloric acid and 0.1 potassium hydroxide, respectively, to pH 6.0, 6.5, 7.0, 7.5 and 8.0, respectively, and diluted to 10 ml. The following precipitation conditions resulted: 0.02 to 0.03 m $PO_4^{3-}$ ($Cl^-$); varying pH; 0.16 μMol CTAB/U pullulanase; 20 to 22 U/ml. The precipitation was affected by the addition of a 10% CTAB solution. The system was stirred for 15 minutes at 0 degrees centigrade. The precipitates were centrifuged off and dissolved in 0.5 m potassium phosphate (pH 7.5). The results are listed in the following table 5.

Table 5

| μMol CTAB/U | pH | U/ml | Activity yield in the precipitate |
|---|---|---|---|
| 0.16 | 8.0 | 22.5 | 50 |
| 0.16 | 7.5 | 22.1 | 65 |
| 0.16 | 7.0 | 20.3 | 74 |
| 0.16 | 6.5 | 20.3 | 65 |
| 0.16 | 6.0 | 20.0 | 36 |

EXAMPLE 21 (Dependence of the CTAB Precipitation on the Salt Concentration and the Ion Species of the Buffer)

The experiments were carried out in the following manner. In each case 5 ml of a 60 to 70% pure pullulanase solution (about 42 U/ml, salt concentration 0.02 m $PO_4^{3-}$) were brought with a 1 m potassium phosphate solution and a 1 m ammonium sulfate solution (pH 7.0), resp., to a solution volume of 10 ml having a salt concentration in correspondence with a molarity of 0.04, 0.06 and 0.08. The resulting precipitation conditions were as follows: 0.16 μMol CTAB/U pullulanase, 20 to 22 U/ml, pH 7.0 and varying salt concentrations. The precipitation was effected by the addition of a 10% CTAB solution. The system was stirred for 15 minutes at 0 degrees centigrade. The precipitates were centrifuged off and dissolved in 0.5 m potassium phosphate (pH 7.0). The results are listed in the following table 6.

Table 6

| salt concentration | pH | μMol CTAB/U | U/ml | activity yield in precipitate |
|---|---|---|---|---|
| 0.02 m $PO_4^{3-}$ | 7.0 | 0.16 | 20.8 | 80% |
| 0.04 m $PO_4^{3-}$ | 7.0 | 0.16 | 22.0 | 60% |
| 0.06 m $PO_4^{3-}$ | 7.0 | 0.16 | 20.5 | 10% |
| 0.08 m $PO_4^{3-}$ | 7.0 | 0.16 | 23.0 | 2% |
| 0.01 m $PO_4^{3-}$ / 0.01 m $SO_4^{2-}$ | 7.0 | 0.16 | 20.6 | 50% |
| 0.01 m $PO_4^{3-}$ / 0.03 m $SO_4^{2-}$ | 7.0 | 0.16 | 21.1 | 3% |
| 0.01 m $PO_4^{3-}$ / 0.05 m $SO_4^{2-}$ | 7.0 | 0.16 | 19.8 | 2% |

EXAMPLE 22 (Dependents of the Activity Yield and the Specific Activity on the Dissolution of the CTAB Precipitate in Salt Solutions Having Increasing Salt Concentrations)

The experiments were carried out as follows. In each case 10 ml of a dialized top phase (example 11) were brought to a pH of 7.0 and diluted to 15 ml. The precipitation conditions were as follows: 0.02 m $PO_4^{3-}$, pH 7.0, approx. 30 U/ml, approx. 11 U/mg and 0.16 μMol CTAB/U. The precipitation was affected by the addition of a 10% CTAB solution. The system was stirred for 15 minutes at 0 degrees centigrade. The precipitates were centrifuged off and dissolved in potassium phosphate and ammonium sulfate, respectively, having increasing concentrations by stirring for 15 minutes. The results are listed in the following table 7.

Table 7

| salt solution | salt concentration | activity yield | specific activity | remarks |
|---|---|---|---|---|
| $(NH_4)_2SO_4$ | 0.05 m | 13% | 14 U/mg | undissolved residue |
|  | 0.10 m | 60% | 24 U/mg | undissolved residue |
| " | 0.15 m | 65% | 25 U/mg | small undissolved residue |
| " | 0.20 m | 73% | 28 U/mg | small undissolved residue |
| " | 0.25 m | 74% | 27 U/mg | small undissolved residue |
| $(K,H)_3PO_4$ | 0.05 m | 3% | 9 U/mg | undissolved residue |
|  | 0.10 m | 22% | 13 U/mg | undissolved residue |
| " | 0.15 m | 34% | 16 U/mg | undissolved residue |
| " | 0.20 m | 40% | 21 U/mg | undissolved residue |
| " | 0.30 m | 56% | 27 U/mg | small undissolved residue |
| " | 0.40 m | 67% | 28 U/mg | small undissolved residue |
| " | 0.50 m | 73% | 27 U/mg | small undissolved residue |

EXAMPLES 23 TO 26 (CTAB-Precipitation Experiments with Different Starting Solutions)

In the following experiments pullulanase was precipitated in the different starting solutions under the best conditions which had been found out in examples 18 to 22.

(EXAMPLE 23)

Starting solution: 70 ml dialized top phase (Example 11), salt concentration corresponding to 0.02 to 0.03 m $PO_4^{3-}$, pH 7.0, activity 72 U/ml, specific activity after gel-electrophoresis 3.6 U/mg (= 9% pure pullulanase).

The precipitation was effected by the addition of a 10% CTAB solution in correspondence to 0.18 μMol CTAB/U pullulanase. The system was stirred for about two hours at 0 degrees centigrade. The precipitate was centrifuged off and dissolved in 50 ml 0.5 m potassium phosphate (pH 7.5).

The following analytical data were obtained: activity yield 85 U/ml = 80%, specific activity approx. 21 U/mg (= 52%), purification factor 5.8 (purification factor = specific activity in the dissolved precipitate/specific starting activity).

(EXAMPLE 24)

Starting solution: 50 ml dialized top phase (example 11), salt concentration corresponding to 0.03 m $PO_4^{3-}$, pH 7.0, activity 42 U/ml, specific activity after gel electrophoresis 12 U/mg (30%).

The precipitation was affected by the addition of a 10% CTAB solution in correspondence to 0.16 μMol CTAB/U pullulanase. The system was stirred for about one hour at 0 degrees centigrade. The precipitate was centrifuged off and dissolved in 10 ml 0.5 m potassium phosphate (pH 7.5).

The following analytical data were obtained: activity yield 147 U/ml = 70%, specific activity after gel electrophoresis 30 U/mg (= 75%), purification factor 2.5.

When the protease activity was tested only traces were found in the starting material, but the dissolved precipitate after CTAB precipitation did not give any evidence. When the α-amylase activity (Phadebas α-Amylasetest/Pharmacia) was tested a value of 30 U/l = 0.03 U/ml was found in the starting material, but the dissolved precipitate after CTAB precipitation did not give any evidence.

(EXAMPLE 25)

Starting solution: 20 ml dialized top phase (example 11), salt concentration 0.03 m $PO_4^{3-}$, pH 7.0, activity 28 U/ml, specific activity after gel electrophoresis 8.4 U/mg (21%).

The precipitation was affected by the addition of a 10% CTAB solution in correspondence to 0.18 μMol/U pullulanase. The system was stirred for about 15 minutes at 4 degrees centigrade. The precipitate was centrifuged off and dissolved in 20 ml 0.5 m potassium phosphate (pH 7.5).

The following analytical data resulted: activity yield 22.5 U/ml = 80%, specific activity after gel electrophoresis 23 U/mg (= 58%), purification factor 2.8.

(EXAMPLE 26)

Starting solution: 15 ml of a top phase (example 11) had been dialized on Amicon XM 100/XM 300; salt concentration 0.02 m $PO_4^{3-}$, pH 7.5, activity 19 U/ml, specific activity after gel electrophoresis 23 U/mg (= 58%), specific activity according to Lowry 25 U/mg (= 62%).

The precipitation was effected by the addition of a 10% CTAB solution in accordance to 0.16 μMol/U pullulanase. The system was stirred for about 15 minutes at 0 degrees centigrade. The precipitate was centrifuged off and dissolved in 10 ml 0.5 m potassium phosphate (pH 7.5).

The following analytical data were obtained: activity yield 22.8 U/ml = 80%, specific activity after gel electrophoresis 34 U/mg (= 85%), specific activity according to Lowry 36 U/mg (= 90%), purification factor 1.45.

Tests with respect to α-amylase and protease activity were negative.

EXAMPLE 27

The possibility of precipitating pullulanase with different cations of nigrogen bases was examined.

An enzyme solution with the following data was used: activity 20.8 U/ml, salt concentration 0.02 m $PO_4^{3-}$, pH 7.5. In each case the precipitate was dissolved in 0.4 m sodium chloride. In each case a 10% aqueous solution of the precipitation reagents was produced.

The resulting data are listed in the following table 8.

Table 8

| Experiment | precipitation reagent | % activity in the precipitate | % activity in the solution | remarks |
|---|---|---|---|---|
| 1 | tetramethyl ammonium chloride | 0 | 85 | no precipitate |
| 2 | N-dodecyl-pyridinium chloride | 80 | 20 | |
| 3 | N-cetyl-pyridinium chloride | 82 | 6 | |

EXAMPLE 28

In this example the quality of different precipitations of pullulanase with cetyltrimethyl ammonium bromide, N-dodecylpyridinium chloride and N-cetylpyridinium chloride was compared.

As starting solution a solution was used which had been concentrated by ultrafiltration on Amicon XM 100 (about 35 U/ml, about 31% pullulanase in the soluble protein, 0.05 m potassium phosphate, pH 7.5).

In each case the precipitation was affected by the addition of 0.2% (weight/weight) of the precipitation reagent corresponding to 0.15 to 0.20 μMol/U pullulanase. The system was stirred for 15 minutes at about 0 degrees centigrade. The precipitates were dissolved in 0.4 m sodium chloride.

The results are listed in the following table 9.

Table 9

| Precipitation reagent | activity in the precipitate (%) | activity in the solution (%) | pullulanase after gel electrophoresis in the protein precipitate (%) | purification factor |
|---|---|---|---|---|
| cetyltrimethyl ammonium bromide | 53 | 26 | 61 | 1.97 |
| N-dodecylpyridinium chloride | 80 | 20 | 48 | 1.54 |
| N-cetylpyri- | 82 | 6 | 53 | 1.70 |

Table 9-continued

| Precipitation reagent | activity in the precipitate (%) | activity in the solution (%) | pullulanase after gel electrophoresis in the protein precipitate (%) | purification factor |
|---|---|---|---|---|
| dinium chloride | | | | |

With respect to the purification factor the precipitation with CTAB provided the best result. Further experiments gave better yields.

EXAMPLE 29

The separability of a two-phase system containing pullulanase and Klebsiella cells was examined in a disc separator.

For this purpose an aqueous two-phased system containing 10% polyethylene glycol ($\overline{M}$ 4,000) and 2% dextran ($\overline{M}$ 500,000) was separated in a disc separator (α-Laval Gyrotester B). In different experiments with 4 jets the best jet length was found to be 13.5 mm and the best flow rate to be 200 ml/min. For this flow rate the residence time was about 135 seconds. The resulting purity of the top phase was nearly 100%, the purity of the bottom about 82% and the loss of the top phase about 2%.

It was possible to recover about 80% pullulanase having a specific activity of 5 to 8 U/mg.

EXAMPLES 30 TO 35

Brewers yeast was frozen three times at −20 degrees centigrade and thawed at +4 degrees centigrade. The pH was maintained with ammonia at 6.2. The clearly centrifuged supernatant was used as starting solution for aqueous two-phase systems. The phases were separated with laboratory centrifuge (about 5 minutes at 3,800 U/minutes and 1,850 g).

The maltese was determined with the help of the pseudo-substrate 4-nitrophenyl-α-D-glucopyranoside (PNPG) at 30 degrees centigrade by measuring the extinction increase at 400 nm (one unit corresponds to a conversion of 1 μMol PNPG/min at 30 degrees centigrade).

(EXAMPLES 30 TO 31; FIG. 9)

The K value was examined as a function of the phosphate concentration and the polyethylene glycol molecular weight. For this purpose an aqueous polyethylene glycol/dextran system having the total volume of 5 ml, 7% polyethylene glycol ($\overline{M}$ 4,000 and 6,000, respectively), 2.5% dextran (weight/weight; $\overline{M}$ 500,000), about 0.1 ml enzyme solution and a potassium phosphate buffer having a pH of 6.8 were used. The results are graphically plotted in FIG. 9.

(EXAMPLES 32 TO 33; FIG. 10)

The examples 30 to 31 were repeated with the exception that the examples were carried out in the presence of increasing amounts of potassium chloride and 0.067 m potassium phosphate buffer (pH 6.8). The results are graphically plotted in FIG. 10.

(EXAMPLES 34 TO 35; FIG. 11)

Examples 30 to 31 were repeated with the exception that the examples were carried out in the presence of increasing amounts of sodium sulfate and 0.067 m potassium phosphate buffer (pH 6.8). The results are graphically plotted in FIG. 11.

EXAMPLES 36 TO 38 (FIG. 12)

The K value of maltase was examined as a function of the pH (disintegration compare examples 30 to 35). For this purpose aqueous polyethylene glycol/dextran systems having 7% polyethylene glycol ($\overline{M}$ 4,000) and 2.5% dextran (weight/weight; $\overline{M}$ 500,000) (example 36), 7% polyethylene glycol ($\overline{M}$ 6,000) and 2.5% dextran (weight/weight; $\overline{M}$ 5,000,000) (example 37) and 9% polyethylene glycol ($\overline{M}$ 4,000) and 1.25 % dextran (weight/weight; $\overline{M}$ 500,000) (example 38), resp., and a total volume of about 5 ml in each case, about 0.1 ml enzyme solution and 0.067 m potassium phosphate buffer were used. The results are graphically plotted in FIG. 12.

EXAMPLES 39 TO 40 (FIG. 13)

The K value of maltase as a function of the concentration and the mean molecular weight of the polyethylene glycol used was examined (disintegration compare examples 30 to 35). For this purpose an aqueous polyethylene glycol/dextran system, having a total volume of about 5 ml, increasing amounts of polyethylene glycol ($\overline{M}$ 4,000 and 6,000 respectively), 2.5% dextran (weight/weight; $\overline{M}$ 500,000), about 0.1 ml enzyme solution and 0.067 m potassium phosphate buffer (pH 6.8) were used. The results are graphically plotted in FIG. 13.

EXAMPLES 41 TO 42 (FIG. 14)

Figure 14:
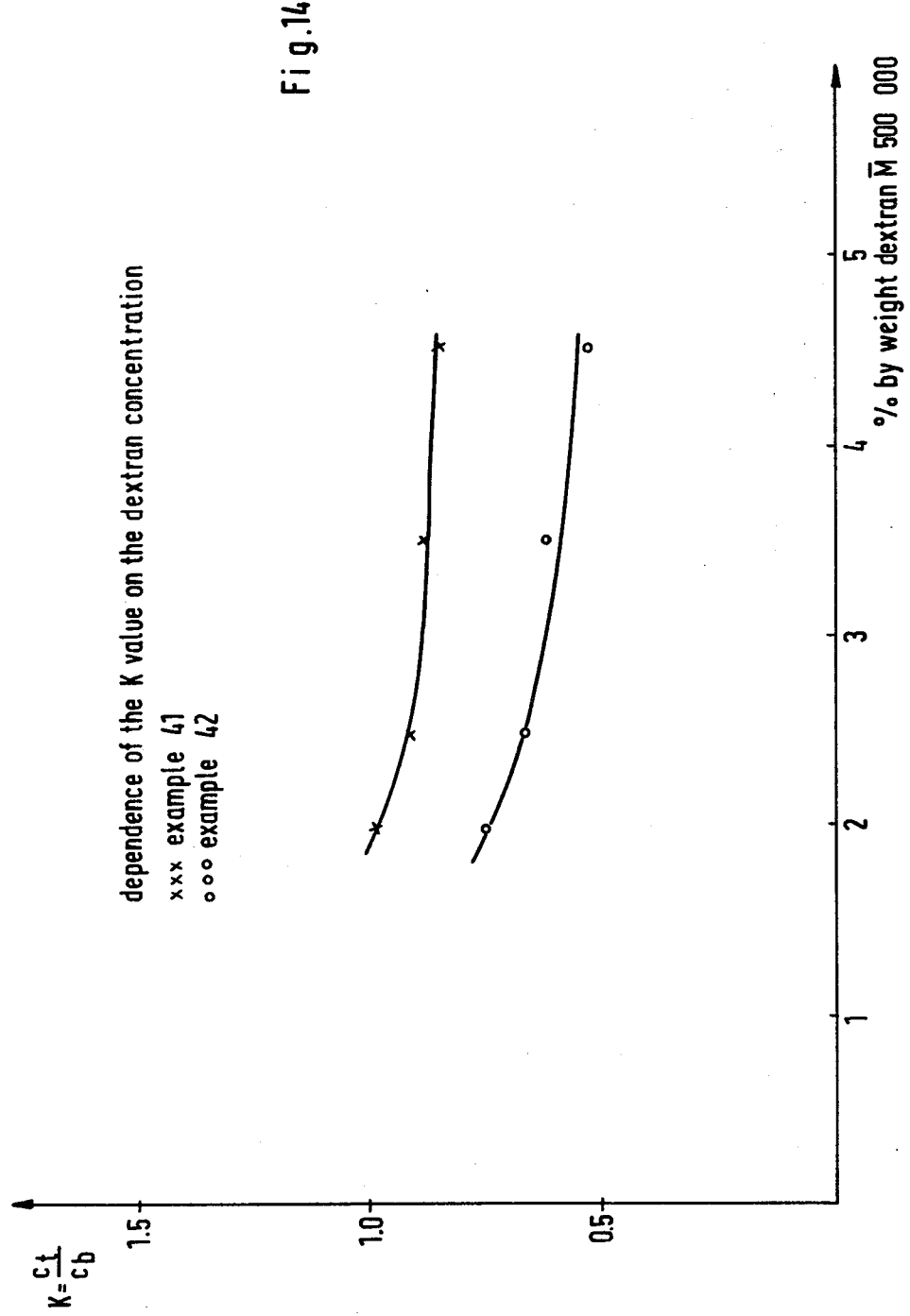
FIG. 14 shows the dependence of the distribution-coefficient K for maltase upon the concentration of dextran and the mean molecular weight of the polyethyleneglycol in aqueous polyethyleneglycol/dextran systems.

The K value of maltase was examined as a function of the dextran concentration and the mean molecular weight of the polyethylene glycol used (disintegration compare examples 30 to 35). For this purpose aqueous polyethylene glycol/dextran systems, having a total volume of about 5 ml, 7% polyethylene glycol (weight/weight; $\overline{M}$ 4,000 and 6,000, respectively), increasing dextran amounts (weight/weight; $\overline{M}$ 500,000), about 0.1 ml enzyme solution and 0.067 m potassium phosphate buffer (pH 6.8) were used. The results are graphically plotted in FIG. 14.

EXAMPLE 43 (FIGS. 15 TO 16)

The K value and the activity yield of maltese were examined as a function of the proportion of cell mass in the total charge.

For this purpose brewers yeast was thawed and frozen four times (activity about 47,143 m U/g). Aqueous polyethylene glycol/dextran systems, having a total volume of about 5 ml, 9% polyethylene glycol ($\overline{M}$ 4,000), 2% dextran (weight/volume; $\overline{M}$ 500,000) and 0.5 m potassium phosphate buffer were used. The pH was about 7.2. The cell amount varied. The results are listed in the following table 10.

Figure 15:
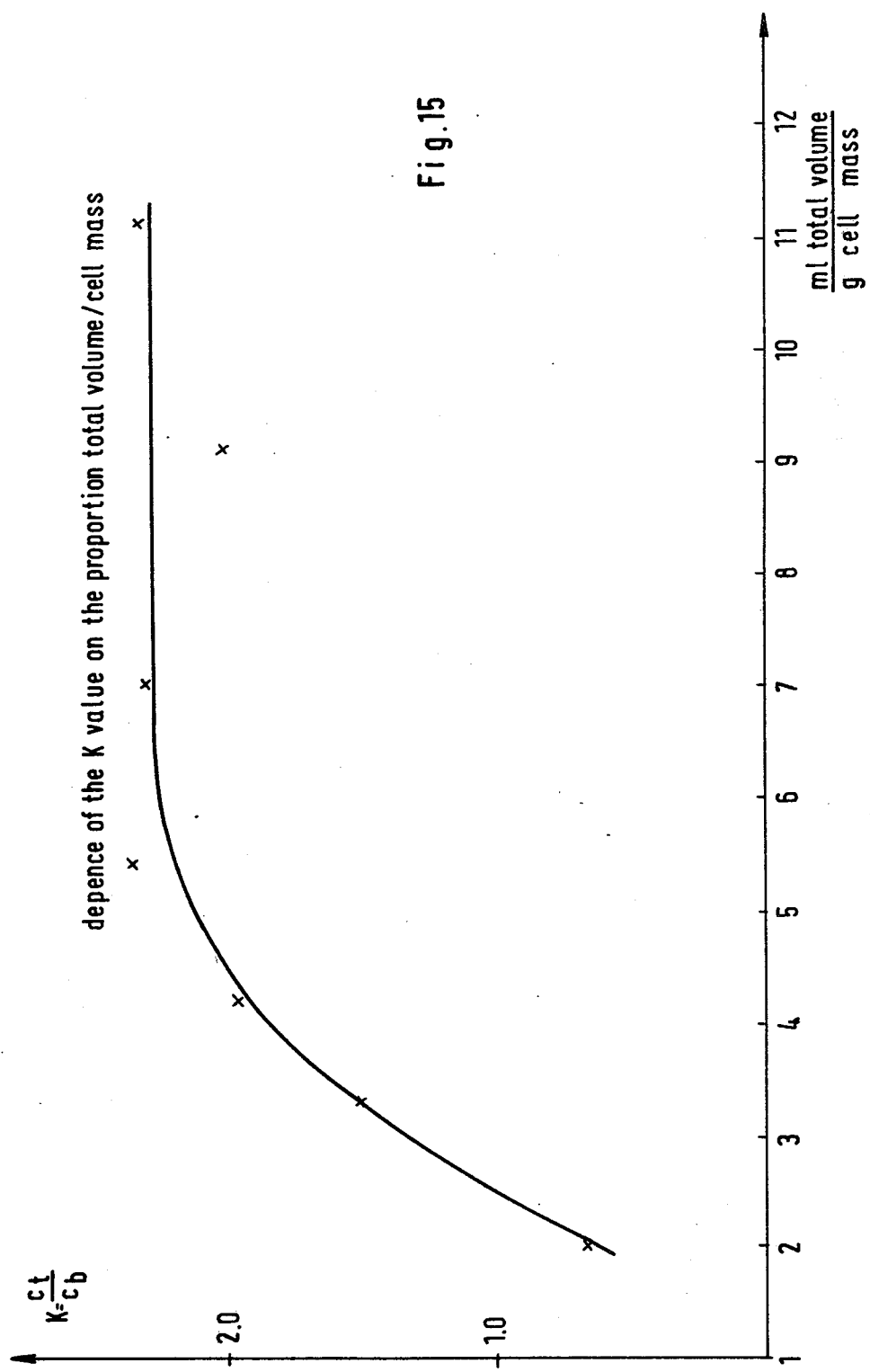
FIG. 15 shows the dependence of the distribution-coefficient K for maltase upon the proportion of cellmass in the whole system in an aqueous polyethyleneglycol/dextran-system.
Figure 16:
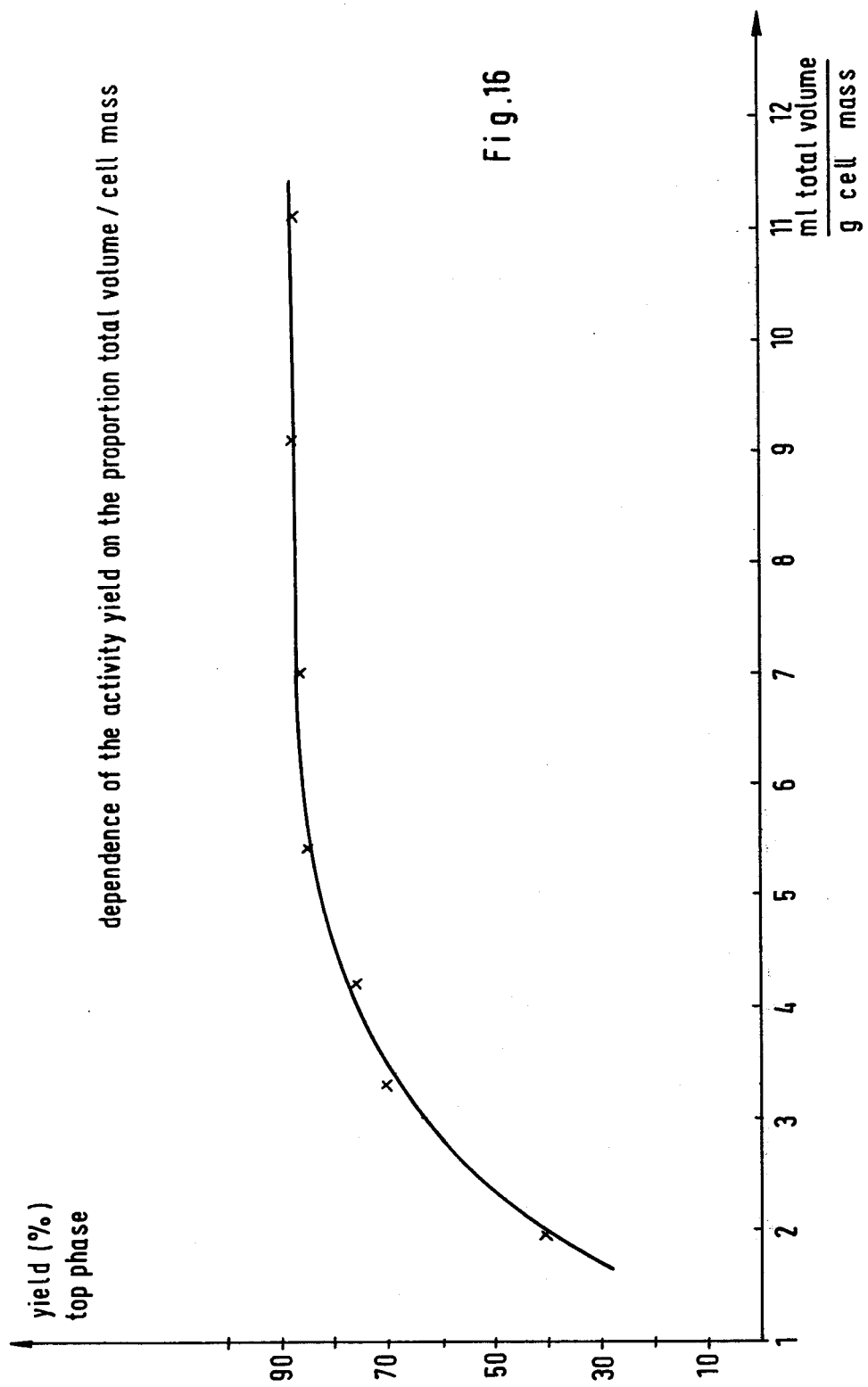
FIG. 16 shows the dependence of the activity yield upon the proportion of cellmass in the whole system in an aqueous polyethyleneglycol/dextran-system.
Figure 17:
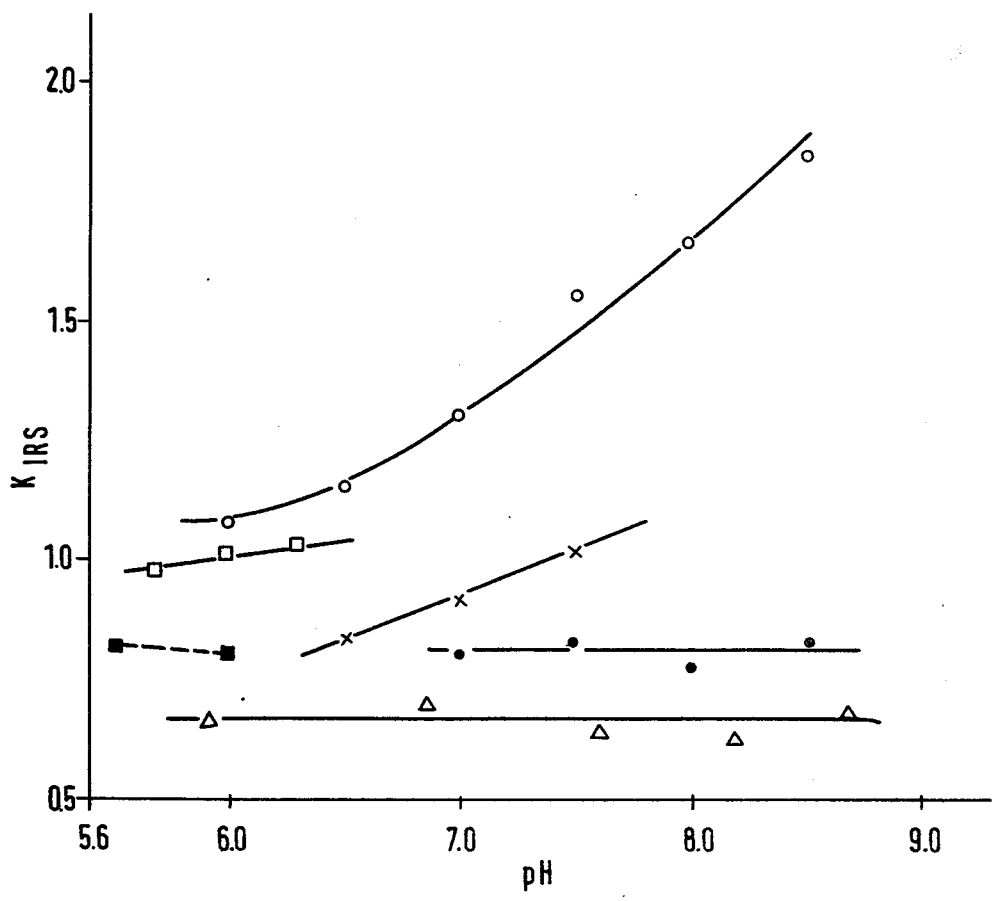
FIGS. 17 to 22 show the dependence of the distribution-coefficient K for isoleucyl-tRNA-synthetase upon different parameters in a two-phase-system containing polyethyleneglycol and dextran.
Figure 18:
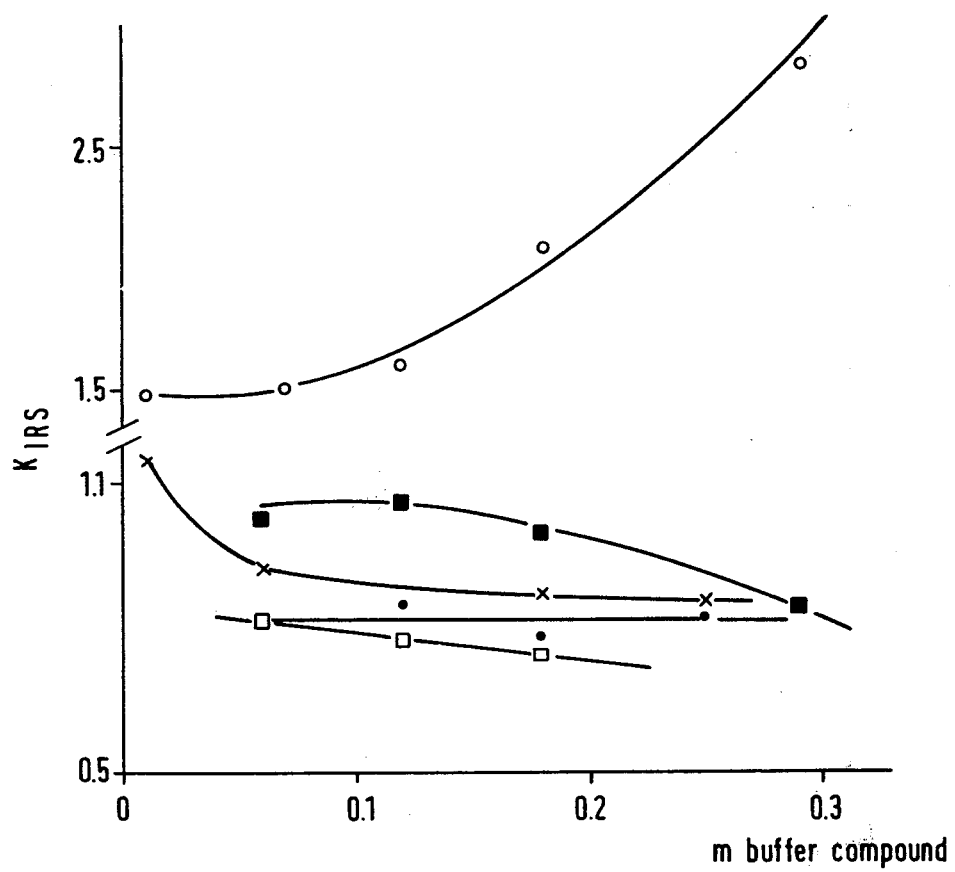
Figure 19:
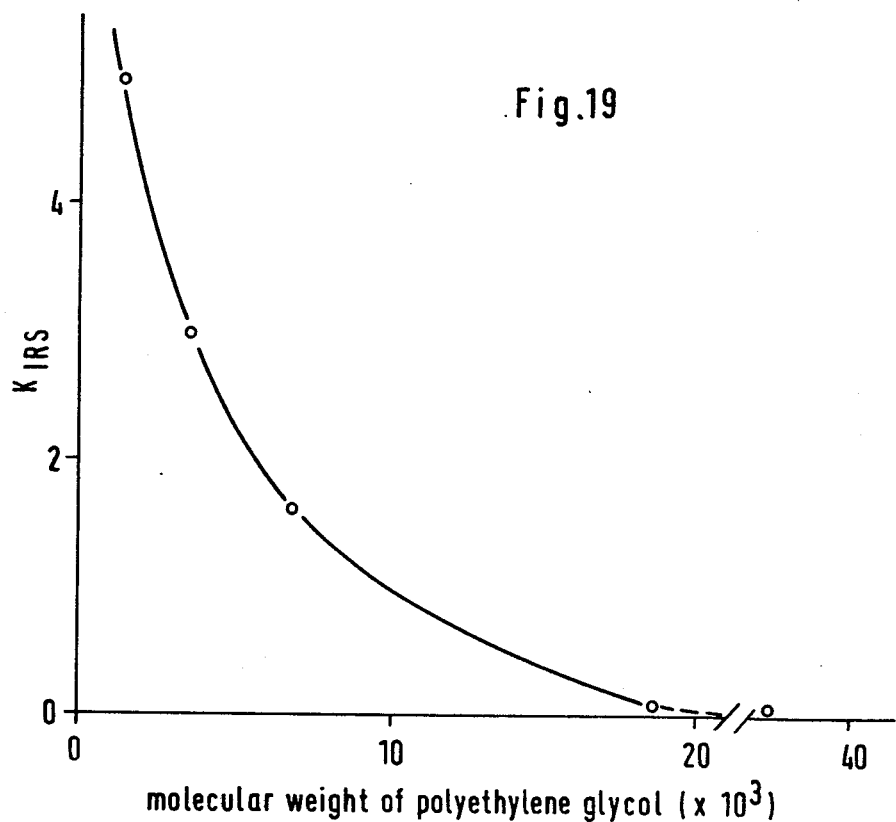
Figure 20:
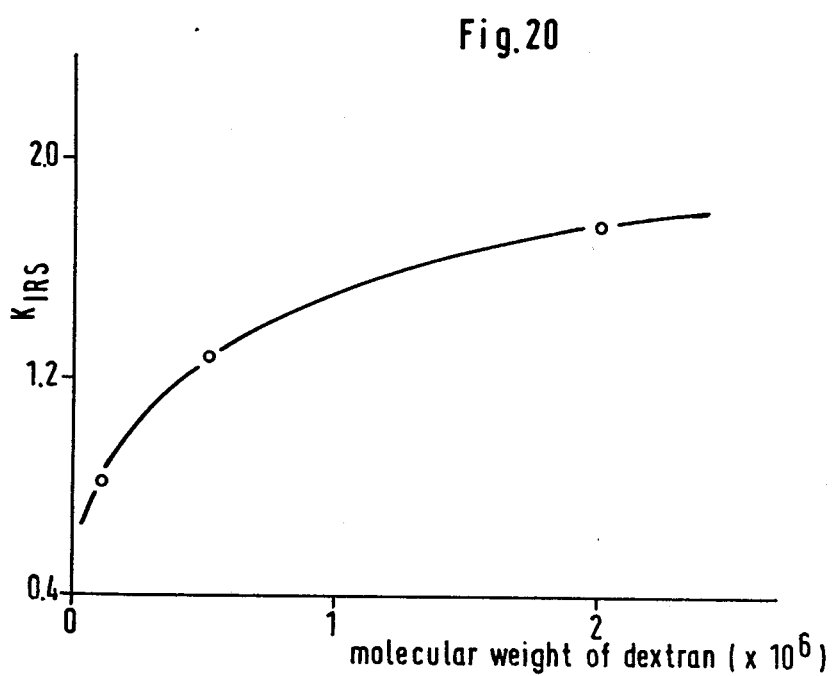
Figure 21:
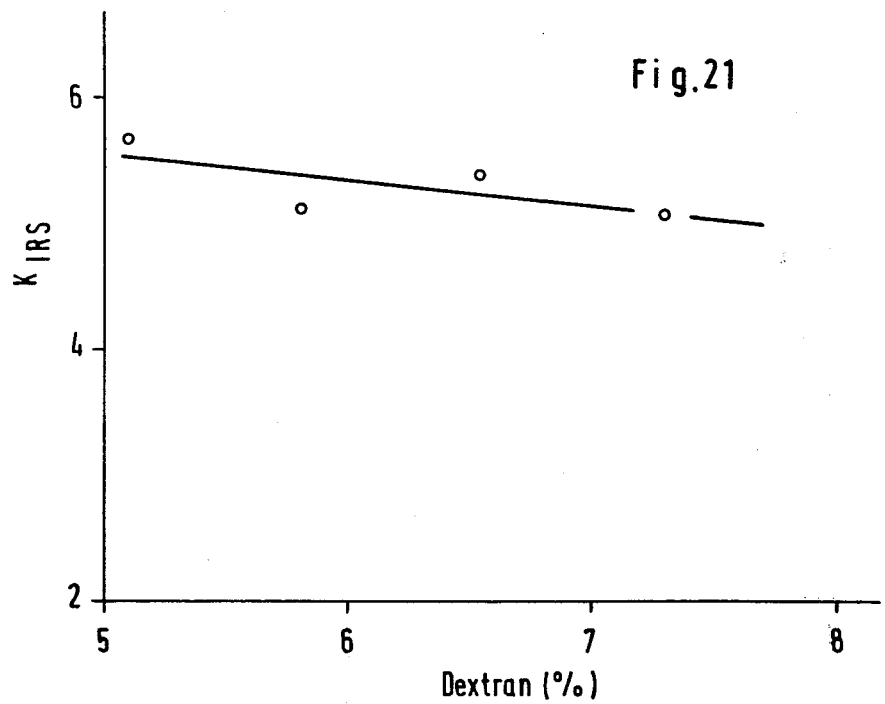
Figure 22:
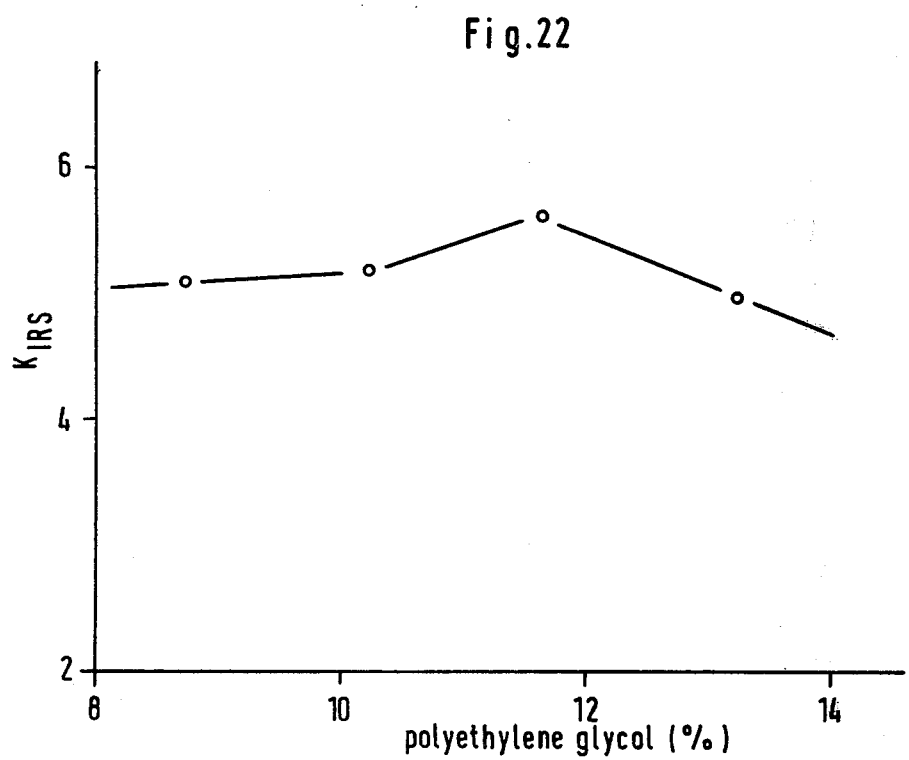

The results demonstrate that for cell proportion in the range of about 20% of the total volume (total volume/cell mass) (ml/g) = 5) an activity yield in the range of 75 to 85% is possible. In every experiment the yeast cells were present in the bottom phase which was still well able to flow. The results are graphically plotted in FIGS. 15 to 16.

Further experiments with freshly prepared yeast resulted in an even better volume-ratio.

Table 10
K value and activity yield of maltase as function of the ratio total volume/weight of cell mass fed

| experiment no. | total volume/ cell mass (ml/g) | top phase (ml) | bottom phase (ml) | top phase/ bottom phase (ml/ml) | activity top phase (mU/ml) | activity bottom phase (mU/ml) | $K(\frac{C_t}{C_b})$ | yield in the top phase (%) |
|---|---|---|---|---|---|---|---|---|
| 1 | 11.1 | 3.7 | 1.3 | 2.85 | 5000 | 2143 | 2.33 | 87.2 |
| 2 | 9.1 | 3.6 | 1.5 | 2.40 | 6429 | 3214 | 2.00 | 87.7 |
| 3 | 7.0 | 3.5 | 1.5 | 2.33 | 8215 | 3571 | 2.30 | 86.0 |
| 4 | 5.4 | 3.6 | 1.8 | 2.00 | 11071 | 4714 | 2.35 | 85.0 |
| 5 | 4.2 | 3.3 | 2.0 | 1.65 | 13572 | 6929 | 1.96 | 76.0 |
| 6 | 3.3 | 3.4 | 2.2 | 1.55 | 16429 | 10929 | 1.50 | 70.0 |
| 7 | 2.0 | 2.3 | 2.7 | 0.85 | 15000 | 22857 | 0.66 | 35.0 |

EXAMPLE 44

In this example the separability of an aqueous two-phase system with maltese and disintegrated brewers yeast-cells was examined in a disc separator (α-Laval-Gyro-Tester B).

For this purpose the experiment started with 830 g brewers yeast which had been disintegrated by thawing and freezing three times (229.2 × 10⁶ mU all together). A system having a total volume of 2,500 ml, 9% (224 g) polyethylene glycol ($\overline{M}$ 4,000), 2% (49 g) dextran (weight/volume; $\overline{M}$ 500,000) and 0.5 m potassium phosphate buffer was used. The pH was 7.2.

The experiment was carried out with 4 jets, having a jet length of 13.5 mm, at a flow rate of 200 ml/min and a residence time of 135 seconds at room temperature.

The activity yield of the collected top phase fractions was 74.4% compared to the starting material (theoretically 79%).

EXAMPLE 45

The separability of an aqueous two-phase system with maltase and disintegrated brewers yeast-cells was examined in a disc separator (α-Laval-Gyro-Tester B).

For this purpose the experiment started with 800 g brewers yeast which had been disintegrated by thawing and freezing three times (activity 197.1 × 10⁶ mU all together). An aqueous system, having a total volume of 2.2 l (2,400 g), 9% (216 g) polyethylene glycol ($\overline{M}$ 4,000), 1.75% (weight/weight, 42 g) dextran ($\overline{M}$ 500,000) and 0.5 m potassium phosphate buffer (pH 7.2) were used.

The separator used was provided with four jets having a jet length of 13.5 mm. The flow rate was 200 ml/min and the residence time 135 seconds at room temperature. The activity yield of the collected top phases was 70.8% compared to the starting material (theoretically 73.4%).

Further experiments with 20% cell mass (total volume/cell mass = 5) showed that even better yields can be obtained.

EXAMPLE 46

One kg *Escherichia coli* MRE 600 was suspended in 0.05 m aqueous potassium phosphate (pH 8.0) and disintegrated twice in a high pressure homogenizer (Manton Gaulin) at 600 kg/cm². Protein concentration was 47.2 mg/ml. This disintegrated material was used for different experiments details of which are given in table 11.

According to the phase diagram of the polyethylene glycol ($\overline{M}$ 6,000)/potassium phosphate system no phase separation should appear under the conditions of experiment 3. It is, however, known that cells or cell fragments as polymers influence these diagrams. In experiment 3 a clear phase separation appeared where the cell fragments went into the highly viscous bottom phase.

EXAMPLE 47

One kg *Escherichia coli* MRE 600 was suspended in 1.4 l (0.05 Mol) aqueous potassium phosphate buffer (pH 8.0) and disintegrated as in example 46. 656 g of 50% polyethylene glycol solution ($\overline{M}$ 6,000) and 525 g of a 50% dipotassium hydrogen phosphate solution (pH 7.8) were added to the suspension. The phases were separated in a disc separator (α-Laval-Gyro-Tester B), having a jet length of 14.5 mm and a flow rate of 160 ml/min and a residence time of 169 seconds.

Table 11

| experiment | polyethylene glycol (%) | $\overline{M}$ | dextran (%) | $\overline{M}$ | K₂HPO₄ (%) | top phase (ml) | bottom phase (ml) | yield of Isoleucyl-tRNA-synthetase (%) |
|---|---|---|---|---|---|---|---|---|
| 1 | 17 | 1550 | 4 | 2,000,000 | — | 7.5 | 2.3 | 16 |
| 2 | 17 | 1550 | 3 | 2,000,000 | — | 7.7 | 2.1 | 21 |
| 3 | 10 | 6000 | — | — | 8 | 7.4 | 1.9 | 96 |

A good separation of the cell fragments at a good enzyme yield and parallel improvement of the specific activity by the factor of about 2 resulted. Details are given in the following table 12.

Table 12

| sample | volume (ml) | protein (mg/ml) | (%) | activity (%) IRS | activity (%) LRS | activity (%) PRS |
|---|---|---|---|---|---|---|
| crude extract | 2100 | 41.6 | 100 | 100 | 100 | 100 |
| top phase | 2640 | 16.4 | 49 | 82 | 82 | 100 | abbreviations:
IRS = isoleucyl-tRNA-synthetase
LRS = leucyl-tRNA-synthetase
PRS = phenylalanyl-tRNA-synthetase

EXAMPLE 48

500 g *Escherichia coli* was suspended in 700 ml aqueous 0.05 m potassium buffer (pH 8.0) and disintegrated by passing a glass bead mill (Dynomuhle von Bachofen; glass pearls 0.25 to 0.5 mm, 5 l/h, 3000 Upm). The resulting suspension was adjusted to 10% polyethylene glycol ($\overline{M}$ 6,000) and 8% potassium phosphate (pH 7.8) and separated in a separator according to example 47.

Again a good separation of the cell fragments from the top phase at a high enzyme yield and an improvement of the specific activity by the factor 2 resulted. Details are listed in the following table 13.

Table 13

| sample | volume (ml) | protein (mg/ml) | (%) | activity (%) | | |
|---|---|---|---|---|---|---|
| | | | | IRS | LRS | PRS |
| crude extract | 1050 | 44.0 | 100 | 100 | 100 | 100 |
| top phase | 1600 | 12.4 | 43 | 93 | 75 | 86 | abbreviations:
IRS = isoleucyl-tRNA-synthetase
LRS = leucyl-tRNA-synthetase
PRS = phenylalanyl-tRNA-synthetase

EXAMPLES 49 TO 54

The distribution coefficient K of isoleucyl-tRNA-synthetase was examined as a function of different parameters in an aqueous two-phase system containing polyethylene glycol and dextran.

(EXAMPLE 49; FIG. 17)

The distribution coefficient K was examined as a function of the pH in the presence of different buffers. For this purpose a two phase system containing 5.0% polyethylene glycol ($\overline{M}$ 6,000), 5.0% dextran ($\overline{M}$ 500,000), 2 mmolar DTE, 1.5 μmolar isoleucyl-tRNA-synthetase and 0.06 m buffer (potassium phosphate, sodium citrate, Tris-maleate, sodium cacodylate, sodium acetate and Tris/HCl, respectively) was used.

In the case of potassium phosphate and sodium cacodylate buffers the K value increases with the increasing pH. In the presence of other buffers the K value is independent of the pH. From this follows that the pH is not the only parameter which influences the partition of the enzyme.

(EXAMPLE 50; FIG. 18)

The distribution coefficient K was examined as a function of the concentration of different buffer ions. For this purpose a system was examined which contained 5.0% polyethylene glycol ($\overline{M}$ 6,000), 5.0% dextran ($\overline{M}$ 500,000), 2 mmolar DTE, 1.5 μmolar isoleucyl-tRNA-synthetase and the following buffers: potassium phosphate (pH 7.5), sodium citrate (pH 6.3), sodium cacodylate (pH 7.0), Tris/HCl (pH 7.0) and sodium acetate (pH 6.0).

The K value increases only with the increasing concentration of the phosphate buffer; in the case of other buffers it is practically independent of the buffer concentration.

(EXAMPLE 51; FIG. 19)

The distribution coefficient K was examined as a function of the average molecular weight of polyethylene glycol. For this purpose a system was used which contained 9.2% polyethylene glycol, 6.3% dextran ($\overline{M}$ 2,000,000), 73 mmolar potassium phosphate (pH 7.0), 2 mmolar DTE and 3.4 μmolar isoleucyl-tRNA-synthetase.

In the case of a mean molecular weight of polyethylene glycol of less than 20,000 the K value increases with the decreasing molecular weight. The enzyme prefers more and more the polyethylene glycol-rich phase when the molecular weight of the polyethylene glycol decreases.

(EXAMPLE 52; FIG. 20)

The distribution coefficient K was examined as a function of the mean molecular weight of dextran. For this purpose a system was examined which contained 9.2% polyethylene glycol ($\overline{M}$ 6,000), 6.2% dextran, 73 mmolar potassium phosphate (pH 7.0), 2 mmolar DTE and 3.4 μmolar isoleucyl-tRNA-synthetase.

The molecular weight of dextran influences the K value just as that of the polyethylene glycol does, however, the K value increases with the increasing molecular weight of dextran.

(EXAMPLES 53 TO 54; FIGS. 21 TO 22)

The distribution coefficient K was examined as a function of the dextran concentration and the polyethylene glycol concentration. For this purpose a two phase system was used which contained 10.2% polyethylene glycol ($\overline{M}$ 1,550), dextran ($\overline{M}$ 2,000,000), 73 mmolar potassium phosphate (pH 7.0), 2 mmolar DTE and 2.8 μmolar isoleucyl-tRNA-synthetase and a two phase system containing polyethylene glycol ($\overline{M}$ 1,550), 6.3% dextran ($\overline{M}$ 2,000,000), 73 mmolar potassium phosphate (pH 7.0), 2 mmolar DTE and 2.8 μmolar isoleucyl-tRNA-synthetase, respectively.

The concentration of the high molecular weight compounds was not found to influence the distribution coefficient K in the examined ranges remarkably.

EXAMPLE 55

The K value of pullulanase was examined as a function of the proportion of the cell mass in the whole charge for aqueous two phase systems.

For this purpose frozen Klebsiella cells were treated as usual and then phosphate buffer, polyethylene glycol ($\overline{M}$ 4,000) and dextran ($\overline{M}$ 500,000) were added. The phosphate concentration was 0.3 m. Then the system was centrifuged. The results are listed in the following table 14.

When the cell mass is present in an amount of about 25% or more a decrease of the K value is noticed. In addition the volume ratio changes in favor of the bottom phase so that a larger activity loss results.

Therefore, a cell mass concentration of about 25 to 30% seems to be reasonable, since in this range the viscosity increase is limited and with the use of separators a greater performance is possible than in the case of larger cell mass concentrations. From the data of table 14 follows for a suspension containing about 25% cell mass (phosphate buffer: cell mass = 3) approximately the following yield: $100/(1 + V_b/V_tK) = 100/1.123 = 90\%$.

Table 14

| polyethylene glycol (%) | dextran (%) | top phase (ml) | bottom phase (ml) | top phase/ bottom phase | K value (0.3 m phosphate) | phosphate buffer/ cell mass (parts/ parts) | total volume/ cell mass (ml/g) |
|---|---|---|---|---|---|---|---|
| 9 | 2 | 4.6 | 5.4 | 0.85 | 1.92 | 0.7 | 2.0 |
| 9 | 2 | 5.5 | 3.7 | 1.5 | 2.00 | 1.0 | 2.6 |
| 9 | 2 | 6.0 | 3.4 | 1.7 | 2.69 | 1.4 | 3.2 |

Table 14-continued

| polyethylene glycol (%) | dextran (%) | top phase (ml) | bottom phase (ml) | top phase/ bottom phase | K value (0.3 m phosphate) | phosphate buffer/ cell mass (parts/ parts) | total volume/ cell mass (ml/g) |
|---|---|---|---|---|---|---|---|
| 9 | 2 | 6.9 | 3.3 | 2.1 | 2.66 | 2.0 | 3.9 |
| 9 | 2 | 6.8 | 2.8 | 2.4 | 3.06 | 2.5 | 4.6 |
| 9 | 2 | 7.0 | 2.4 | 2.9 | 2.96 | 3.0 | 5.3 |
| 9 | 2 | 7.8 | 2.5 | 3.1 | 2.80 | 4.0 | 6.6 |
| 9 | 2 | 8.0 | 2.3 | 3.5 | 3.00 | 5.5 | 8.5 |
| 9 | 2 | 8.65 | 1.05 | 8.2 | — | no cell mass | |

EXAMPLES 56 TO 57

The distribution coefficient K of pullulanase was examined as a function of different parameters in an aqueous two phase system containing polyethylene glycol and ammonium sulfate.

(EXAMPLE 56)

The experiment was started with polyethylene glycol ($\overline{M}$ 4,000, 50% aqueous solution), solid ammonium sulfate and in each case 5 ml enzyme solution (purity 60%, pH 7.5, a salt concentration of about 0.02 m $PO_4^{3-}$) to form a two phase system. The different values are listed in table 15.

Table 15

| $(NH_4)_2SO_4$ (% weight/ weight) | Polyethylene glycol ($\overline{M}$ 4000; % weight/ weight) | K value | activity yield in the salt phase (%) | top phase (ml) | bottom phase (ml) |
|---|---|---|---|---|---|
| 8.5 | 16 | 0.37 | 56.5 | — | — |
| 8.5 | 18 | 0.40 | 45.5 | 3.6 | 1.1 |
| 9.5 | 14 | 0.37 | 60.4 | 3.0 | 1.8 |
| 9.5 | 16 | 0.47 | 52.8 | 3.1 | 1.7 |
| 9.5 | 18 | 0.51 | 48.2 | 3.3 | 1.5 |
| 11 | 11 | 0.33 | 79.0 | 2.2 | 2.5 |
| 11 | 12 | 0.38 | 69.4 | 2.4 | 2.3 |
| 11 | 14 | 0.39 | 66.9 | 2.6 | 2.1 |
| 11 | 16 | 1.08 | 43.3 | 2.4 | 2.2 |
| 11 | 18 | 2.38 | 23.2 | 2.6 | 2.1 |
| 12 | 8 | 0.28 | 88.2 | 1.5 | 3.2 |
| 12 | 9 | 0.27 | 84.6 | 1.6 | 3.1 |
| 12 | 10 | 0.29 | 77.6 | 1.8 | 2.8 |
| 12 | 12 | 0.73 | 52.8 | 2.0 | 2.7 |
| 12 | 14 | 0.93 | 44.2 | 2.1 | 2.5 |
| 12 | 16 | 1.10 | 30.1 | 2.2 | 2.4 |
| 12 | 18 | 9.36 | 7.8 | 2.3 | 2.3 |

(EXAMPLE 57)

The experiment was started with polyethylene glycol ($\overline{M}$ 4,000, 50% aqueous solution), solid ammonium sulfate, in each case 5 ml enzyme solution (purity 60%, pH 7.5, salt concentration about 0.02 m $PO_4^{3-}$) and a potassium phosphate buffer (pH 7.5) to form a two phase system. The different values are listed in table 16.

Table 16

| $(NH_4)_2SO_4$ (% weight/ weight) | Polyethylene glycol ($\overline{M}$ 4000; % weight/ weight | potassium phosphate (mmol.) | K value | activity yield in the salt phase (%) | top phase (ml) | bottom phase (ml) |
|---|---|---|---|---|---|---|
| 9.5 | 14 | — | 0.38 | 58.5 | 3.0 | 1.6 |
| 9.5 | 14 | 10 | 0.29 | 69.9 | 2.8 | 1.9 |
| 9.5 | 14 | 20 | 0.42 | 62.9 | 2.8 | 2.0 |
| 9.5 | 14 | 30 | 0.31 | 72.5 | 2.6 | 2.1 |
| 9.5 | 14 | 50 | 0.40 | 67.1 | 2.6 | 2.1 |
| 9.5 | 14 | 100 | 0.88 | 52.1 | 2.4 | 2.3 |
| 9.5 | 14 | 200 | 6.47 | 12.9 | 2.3 | 2.3 |
| 9.5 | 14 | 300 | 42.63 | 1.1 | 2.1 | 2.6 |

From tables 15 to 16 it is clear that the pullulanase dissolves to a greater extent in the polyethylene glycol containing top phase when the ammonium sulfate and polyethylene glycol concentration increases. Furthermore, a greater increase of the K value can be observed when the phosphate concentration increases.

EXAMPLE 58

In this example the recovery of phosphorylase with the use of an aqueous polyethylene glycol/dextran system is described.

For this purpose a bottom phase (0.65 kg cell mass/l) resulting from the pullulanase isolation according to examples 11 and 55, respectively is diluted with water in a ratio of 1:2; 5 mg DNAase/l, if desired, added to decompose the DNA enzymatically; then the system is stirred for some hours and finally, disintegrated in a homogenizator (Manton-Gaulin) at a pressure of 600 kg/cm². The phosphorylase activity was 11 U/ml, the protein content 19 mg/ml and the specific acitivity 0.6 U/mg.

A two phase system was formed by mixing the following components in the indicated amounts:

| | |
|---|---|
| 2.0 ml | diluted bottom phase of the pullulanase separation (example 11) after disintegration |
| 0.9 ml | 50% polyethyleneglycol ($\overline{M}$ 1550) |
| 0.6 ml | (5 m) NaCl |
| 0.5 ml | (2.5 m) $K_2HPO_4$ (pH 9.4) |
| 0.7 ml | water with 5 µl β-mercaptoethanol |
| 4.7 ml | resulting mixture (pH about 7.8) |

The suspension was vigorously mixed for 1.5 minutes and centrifuged at about 4,000 g for 10 minutes. 3.4 ml clear top phase and 1.3 ml bottom phase resulted, which contained the cell fragments. The phosphorylase activity in the top phase was 5.5U/ml, the protein content 7.7 mg/ml, the specific activity 0.7 U/mg, the enrichment about 1.2 and the yield 84%.

Abbreviations Used

Ficoll = synthetic polysaccharide formed by polymerising saccharose, $\overline{M}$ about 400,000;
dextran = polysaccharid from glucose, empirical formula $(C_6H_{10}O_5)_x$;
Tris = tris-(hydroxymethyl)-aminomethan;
DEAE-dextran = diethylaminoethyl-dextran;
DEAE-cellulose = diethylaminoethyl-cellulose;
U = enzyme unit, i.e. the amount of enzyme which converts 1 µMol substrate to product;
Triton X 100 = octylphenol-polyethyleneglycolether (non-ionic detergent);
EDTA = ethylenediamintetra acetic acid (disodium salt);
CTAB = cethyltrimethylammoniumbromide;
Amicon XM 100 = ultrafiltration membrane, exclusion limit about $\overline{M}$ 100,000 (Amicon Corp.);

Amicon XM 300 = ultrafiltration membrane, exclusion limit about $\overline{M}$ 300,000 (Amicon Corp.).

We claim:

1. A process for the separation of enzymes from cell fragments or intact cells wherein the enzymes are solubilized, the system resulting after said enzyme solubilization which contains the enzymes, insoluble components and cell liquid is fed into an aqueous multiphase system
   (a) containing one high molecular weight compound of the group consisting of unsubstituted or substituted polyalcohols, polyethers, polyesters, polyvinylpyrroldones and polysaccharides and at least one inorganic salt, or
   (b) containing at least two high molecular weight compounds of the group consisting of unsubstituted or substituted polyalcohols, polyethers, polyesters, polyvinylpyrrolidones and polysaccharides, separating the phases from each other, separating the enzymes from the high molecular weight compounds and, if desired, isolating the enzymes.

2. Process according to claim 1, characterized in that high molecular weight compounds of the group consisting of polypropylenglycol, polyethylene glycol, methoxypolyethylene glycol, trimethylaminopolyethylene glycol, polyethylene glycol sulfonate, polyvinylalcohol, polyvinylpyrrolidone, methylcellulose, ethylhydroxyethylcellulose, DEAE-cellulose, alkalimetall carboxymethylcellulose, dextran, hydroxypropyldextran, DEAE-dextran, dextransulfate, alkalimetall carboxymethyldextran and ficoll are used.

3. Process according to claim 1, characterized in that a multiphase system according to (a) is used which contains polyethylene glycol.

4. Process according to claim 1, characterized in that a multiphase system according to (a) is used which contains an unsubstituted or substituted polyalcohol or polyether having an average molecular weight less than 40,000.

5. Process according to claim 1, characterized in that a multiphase system according to (a) is used which contains, as the salt, a sulfate, a phosphate, or combination thereof.

6. Process according to claim 1, characterized in that a multiphase system according to (a) is used which contains a potassium phosphate.

7. A process according to claim 1, characterized in that a multiphase system according to (a) has polyethylene glycol as the high molecular weight compound, the salt is potassium phosphate, and is used for the separation of enzymes of *Escherichia coli*, such as aminoacyl-tRNA-synthetases.

8. Process according to claim 7, characterized in that a system is used which contains water, a high molecular weight compound and salt in such quantities, that these components themselves form only a single phase.

9. Process according to claim 1, characterized in that a multiphase system according to (b) is used which contains polyethylene glycol and dextran.

10. Process according to claim 1, characterized in that a multiphase system according to (b) is used which contains an unsubstituted or substituted polyalcohol or polyether having clearly smaller average molecular weight than the enzyme, preferably an average molecular weight smaller than 40,000.

11. A process according to claim 1, characterized in that a multiphase system according to (b) is used which contains an unsubstituted or substituted polysaccharide having a clearly greater average molecular weight than the enzyme.

12. A process according to claim 1, characterized in that a multiphase system according to (b) with a total content of polyethylene glycol of one and more and prefereably 4 to 9 percent by weight is used.

13. Process according to claim 1, characterized in that a multiphase system according to (b) with a total content of dextran of 0.1 to 15 percent by weight is used.

14. Process according to claim 1 characterized in that a multiphase system according to (b) is used, which, in addition, contains phosphate ions.

15. Process according to claim 14, characterized in that for the separation of pullulanase as the said enzyme a multiphase system according to (b) with a phosphate ion concentration of more than 0.001 m is used.

16. Process according to claim 14, characterized in that for the separation of maltase as the said enzyme a multiphase system according to (b) with a phosphate ion concentration of more than 0.1 m is used.

17. Process according to claim 1, characterized in that a multiphase system with a ratio of total volume/cell mass = 2 is used.

18. Process according to claim 1, characterized in that a multiphase system with a pH of 6 to 9 is used.

19. Process according to claim 1, characterized in that the phases are separated with the use of a separator.

20. Process according to claim 1, characterized in that the high molecular weight compounds are separated from the enzyme by precipitating the enzyme or by phase partition, ultrafiltration, dialysis, gelpermeation, adsorbents, ion exchangers or electrophoresis.

21. Process according to claim 1, characterized in that (optionally after separating the high molecular weight compounds) the pullulanase as the said enzyme is precipitated with a compound of the following general formula:

$$NR^1R^2R^3R^4X,$$

where $R^1$ is an organic group having at least 10 carbon atoms, $R^2$, $R^3$ and $R^4$, which may be the same or different, are hydrogen atoms, or organic groups having 1 to 20 carbon atoms, where the organic groups $R^1$ to $R^4$ are selected from the group of alkyl, substituted alkyl, alkenyl, aryl, substituted aryl, aralkyl and saturated and unsaturated cyclic groups, $R^3$ and $R^4$ can form together a cyclic group, where $R^2$ may be missing if the cyclic group is unsaturated and where X is an inorganic or organic anion, e.g. a haloid, phosphate, nitrate, sulfate or acetate ion.

22. Process according to claim 21, characterized in that the pullulanase is precipitated with a dodecylmethylammonium, dodecyltrimethylammonium, tetradecylammonium, cetylmethylammonium, cetyldimethylammonium, cetyltrimethylammonium, octadecyltrimethylammonium, benzyldodecyldimethylammonium, N, N-diethylmorpholinium, cetylpyridinium, decenyltrihydroxyethylammonium, dioctadecyldiethylammonium, dioctadecylmorpholimium, dilauryldimethylammonium, or disteraryl-2-chlorethylbutylammonium compound.

23. Process according to claim 4 wherein the polyalcohol or polyether has an average molecular weight less than 10,000.

24. Process according to claim 5 wherein said sulfate salt is an alkali metal sulfate and said phosphate is an alkali metal phosphate.

25. Process according to claim 10 wherein the polyalcohol or polyether has a molecular weight below 10,000.

26. Process according to claim 25 wherein the polyglycol or polyether has a molecular weight below 6,000.

27. Process according to claim 26 wherein the polyglycol or polyether has a molecular weight between 5,000 to 1,550.

28. Process according to claim 27 wherein the polyglycol or polyether has a molecular weight of about 4,000.

29. Process according to claim 12 wherein the total content of polyethylene glycol is in the range of 4 go 9 percent by weight.

30. Process according to claim 13 wherein the total content of dextran is in the range of from 0.1 to 7 percent by weight.

31. Process according to claim 15 wherein the phosphate ion concentration is more than 0.005.

32. Process according to claim 31 wherein the phosphate ion concentration is more than 0.02 m.

33. Process according to claim 16 wherein the phosphate ion concentration is more than 0.3 m.

34. Process according to claim 33 wherein the phosphate ion concentration is more than 0.5 m.

35. Process according to claim 17 wherein the total volume/cell mass equals 5.

36. Process according to claim 18 wherein the pH is 7 to 8.

37. Process according to claim 21 wherein $R_1$ is an organic group of from 10 to 20 carbon atoms, $R^2$, $R^3$ and $R_4$ may be the same or different organic groups having 1 to 6 carbon atoms.

* * * * *